(12) United States Patent
Shuber et al.

(10) Patent No.: US 6,475,738 B2
(45) Date of Patent: *Nov. 5, 2002

(54) METHODS FOR DETECTING MUTATIONS USING PRIMER EXTENSION FOR DETECTING DISEASE

(75) Inventors: Anthony P. Shuber, Milford, MA (US); William Pierceall, Wellesley, MA (US)

(73) Assignee: Exact Sciences Corporation, Maynard, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/883,548

(22) Filed: Jun. 18, 2001

(65) Prior Publication Data

US 2002/0064787 A1 May 30, 2002

Related U.S. Application Data

(60) Division of application No. 09/757,949, filed on Jan. 10, 2001, which is a continuation-in-part of application No. 09/468,670, filed on Dec. 21, 1999, now abandoned, and a continuation-in-part of application No. 09/371,991, filed on Aug. 11, 1999, now Pat. No. 6,280,947.
(60) Provisional application No. 60/134,711, filed on Jan. 10, 1999.

(51) Int. Cl.[7] .................... C12Q 1/68; C12P 19/34
(52) U.S. Cl. .................... 435/6; 435/91.2
(58) Field of Search .................... 435/6, 91.2

(56) References Cited

U.S. PATENT DOCUMENTS

| | | | |
|---|---|---|---|
| 4,101,279 A | 7/1978 | Aslam | 23/259 |
| 4,309,782 A | 1/1982 | Paulin | 4/661 |
| 4,333,734 A | 6/1982 | Fleisher | 23/230 |
| 4,445,235 A | 5/1984 | Slover et al. | 4/144.2 |
| 4,535,058 A | 8/1985 | Weinberg et al. | 435/6 |
| 4,683,195 A | 7/1987 | Mullis et al. | 435/6 |
| 4,705,050 A | 11/1987 | Markham | 128/749 |
| 4,735,905 A | 4/1988 | Parker | 436/174 |
| 4,786,718 A | 11/1988 | Weinberg et al. | 530/387 |
| 4,857,300 A | 8/1989 | Maksem | 424/3 |
| 4,871,838 A | 10/1989 | Bos et al. | 536/27 |
| 4,981,783 A | 1/1991 | Augenlicht | 435/6 |
| 4,982,615 A | 1/1991 | Sultan et al. | 73/864.51 |
| 5,087,617 A | 2/1992 | Smith | 514/44 |
| 5,126,239 A | 6/1992 | Livak et al. | 435/6 |
| 5,137,806 A | 8/1992 | LeMaistre et al. | 435/6 |
| 5,149,506 A | 9/1992 | Skiba et al. | 422/102 |
| 5,196,167 A | 3/1993 | Guadagno et al. | 422/56 |
| 5,202,231 A | 4/1993 | Drmanac et al. | 435/6 |
| 5,248,671 A | 9/1993 | Smith | 514/44 |
| 5,272,057 A | 12/1993 | Smulson et al. | 435/6 |
| 5,302,509 A | 4/1994 | Cheeseman | 435/6 |
| 5,330,892 A | 7/1994 | Vogelstein et al. | 435/6 |
| 5,331,973 A | 7/1994 | Fiedler et al. | 128/760 |
| 5,348,855 A | 9/1994 | Dattagupta et al. | 435/6 |
| 5,352,775 A | 10/1994 | Albertsen et al. | 536/23.1 |
| 5,362,623 A | 11/1994 | Vogelstein et al. | 435/6 |
| 5,369,004 A | 11/1994 | Polymeropoulos et al. | 435/6 |
| 5,378,602 A | 1/1995 | Polymeropoulos et al. | 435/6 |
| 5,380,645 A | 1/1995 | Vogelstein | 435/6 |
| 5,380,647 A | 1/1995 | Bahar | 435/7.23 |
| 5,382,510 A | 1/1995 | Levine et al. | 435/6 |
| 5,409,586 A | 4/1995 | Kamahori et al. | 204/182.8 |
| 5,458,761 A | 10/1995 | Kamahori et al. | 204/299 |
| 5,463,782 A | 11/1995 | Carlson et al. | 4/661 |
| 5,466,576 A | 11/1995 | Schulz et al. | 435/6 |
| 5,468,610 A | 11/1995 | Polymeropoulos et al. | 435/6 |
| 5,468,613 A | 11/1995 | Erlich et al. | 435/6 |
| 5,489,508 A | 2/1996 | West et al. | 435/6 |
| 5,492,808 A | 2/1996 | de la Chapelle et al. | 435/6 |
| 5,496,470 A | 3/1996 | Lenhart | 210/222 |
| 5,508,164 A | 4/1996 | Kausch et al. | 435/6 |
| 5,512,441 A | 4/1996 | Ronal | 435/6 |
| 5,514,547 A | 5/1996 | Balazs et al. | 435/6 |
| 5,527,676 A | 6/1996 | Vogelstein et al. | 435/6 |
| 5,532,108 A | 7/1996 | Vogelstein | 435/240.2 |
| 5,545,527 A | 8/1996 | Stevens et al. | 435/6 |
| 5,552,283 A | 9/1996 | Diamandis et al. | 435/6 |
| 5,569,584 A | 10/1996 | Augenlicht | 435/6 |
| 5,571,676 A | 11/1996 | Shuber | 435/6 |
| 5,578,458 A | 11/1996 | Caskey et al. | 435/6 |
| 5,580,729 A | 12/1996 | Vogelstein | 435/6 |
| 5,589,335 A | 12/1996 | Kearney et al. | 435/6 |
| 5,610,287 A | 3/1997 | Nikiforov et al. | 536/29.3 |
| 5,616,463 A | 4/1997 | Fornace, Jr. et al. | 435/6 |
| 5,627,032 A | 5/1997 | Ulanovsky | 435/6 |
| 5,635,347 A | 6/1997 | Link et al. | 435/6 |
| 5,650,277 A | 7/1997 | Navot et al. | 435/6 |
| 5,670,325 A | 9/1997 | Lapidus et al. | 435/6 |
| 5,709,998 A | 1/1998 | Kinzler et al. | 435/6 |
| 5,741,650 A | 4/1998 | Lapidus et al. | 435/6 |
| 5,759,777 A | 6/1998 | Kearney et al. | 435/6 |
| 5,830,665 A | 11/1998 | Shuber et al. | 435/6 |
| 5,834,193 A | 11/1998 | Kozlowski et al. | 435/6 |

(List continued on next page.)

FOREIGN PATENT DOCUMENTS

| | | |
|---|---|---|
| AU | A-11325/95 | 10/1994 |
| EP | 0 185 494 A2 | 6/1986 |
| EP | 0 284 362 A2 | 9/1988 |

(List continued on next page.)

OTHER PUBLICATIONS

Frangi D et al. Nonsense mutations affect C1 inhibitor messenger RNA levels in patients with type I hereditary angioneurotic edema. J Clin Invest., vol. 88: 755–759, 1995.*

(List continued on next page.)

*Primary Examiner*—Jeffrey Fredman
*Assistant Examiner*—Suryaprabha Chunduru
(74) *Attorney, Agent, or Firm*—Testa, Hurwitz & Thibeault

(57) ABSTRACT

Methods of the invention comprise assays for markers indicative of cancer, precancer, and other diseases or disorders. Assays of the invention are preformed on heterogeneous samples obtained from patients by non-invasive or minimally-invasive methods. Such assays may be employed alone or in combination with other disease screening techniques.

13 Claims, 8 Drawing Sheets

U.S. PATENT DOCUMENTS

| | | | |
|---|---|---|---|
| 5,846,710 A | 12/1998 | Bajaj | 435/6 |
| 5,885,775 A | 3/1999 | Haff et al. | 435/6 |
| 5,888,778 A | 3/1999 | Shuber | 435/91.1 |
| 5,888,819 A | 3/1999 | Goelet et al. | 435/5 |
| 5,928,870 A | 7/1999 | Lapidus et al. | 435/6 |
| 5,945,284 A * | 8/1999 | Livak et al. | 435/6 |
| 6,013,431 A * | 1/2000 | Soderlund et al. | 435/6 |
| 6,153,379 A | 11/2000 | Caskey et al. | 435/6 |
| 6,177,249 B1 * | 1/2001 | Kwok et al. | 435/6 |
| 6,177,251 B1 | 1/2001 | Vogelstein et al. | 435/6 |
| 6,280,947 B1 * | 8/2001 | Shuber et al. | 435/6 |

FOREIGN PATENT DOCUMENTS

| | | |
|---|---|---|
| EP | 0 332 435 A2 | 9/1989 |
| EP | 0 337 498 A2 | 10/1989 |
| EP | 0 390 323 A2 | 10/1990 |
| EP | 0 390 323 A3 | 10/1990 |
| EP | 0 407 789 A1 | 1/1991 |
| EP | 0 407 789 B1 | 1/1991 |
| EP | 0 408 918 A1 | 1/1991 |
| EP | 0 332 435 B1 | 4/1992 |
| EP | 0 497 527 A1 | 8/1992 |
| EP | 0 408 918 B1 | 11/1993 |
| EP | 0 608 004 A2 | 7/1994 |
| EP | 0 259 031 B1 | 11/1994 |
| EP | 0 664 339 A1 | 7/1995 |
| GB | 2 293 238 A | 3/1996 |
| WO | WO 89/11211 | 11/1989 |
| WO | WO 90/09455 | 8/1990 |
| WO | WO 91/13075 | 9/1991 |
| WO | WO 92/13103 | 8/1992 |
| WO | WO 92/15712 | 9/1992 |
| WO | WO 92/16657 | 10/1992 |
| WO | WO 93/06240 | 4/1993 |
| WO | WO 93/18186 | 9/1993 |
| WO | WO 93/20223 | 10/1993 |
| WO | WO 93/20235 | 10/1993 |
| WO | WO 94/00603 | 1/1994 |
| WO | WO 94/01447 | 1/1994 |
| WO | WO 94/09161 | 4/1994 |
| WO | WO 94/10575 | 5/1994 |
| WO | WO 94/11383 | 5/1994 |
| WO | WO 94/23055 | 10/1994 |
| WO | WO 95/00669 | 1/1995 |
| WO | WO 95/07361 | 3/1995 |
| WO | WO 95/09928 | 4/1995 |
| WO | WO 95/09929 | 4/1995 |
| WO | WO 95/12606 | 5/1995 |
| WO | WO 95/12607 | 5/1995 |
| WO | WO 95/13397 | 5/1995 |
| WO | WO 95/15400 | 6/1995 |
| WO | WP 95/16792 | 6/1995 |
| WO | WO 95/18818 | 7/1995 |
| WO | WO 95/19448 | 7/1995 |
| WO | WO 95/20680 | 8/1995 |
| WO | WO 95/25813 | 9/1995 |
| WO | WO 95/31728 | 11/1995 |
| WO | WO 96/01907 | 1/1996 |
| WO | WO 96/02671 | 2/1996 |
| WO | WO 96/06951 | 3/1996 |
| WO | WO 96/08514 | 3/1996 |
| WO | WO 96/12821 | 5/1996 |
| WO | WO 96/13611 | 5/1996 |
| WO | WO 96/30545 | 10/1996 |
| WO | WO 97/09449 | 3/1997 |
| WO | WO 97/09600 | 3/1997 |
| WO | WO 97/22719 | 6/1997 |
| WO | WO 97/23651 | 7/1997 |
| WO | WO 97/25442 | 7/1997 |
| WO | WO 98/13522 | 4/1998 |
| WO | WO 98/38338 | 9/1998 |
| WO | WO 98/58081 | 12/1998 |
| WO | WO 98/58084 | 12/1998 |

OTHER PUBLICATIONS

Iacopetta B et al. Rapid and nonisotopic SSCP–based analysis of the BAT–26 mononucleotide repeat for identification of the replication error phenotype in human cancers. Human Mutation, vol. 12: 355–360, 1998.*

Beskin et al., "On the Mechanism of the Modular Primer Effect," *Nucleic Acids Research*, vol. 23, No. 15, pp. 2881–2885 (1995).

Caetano–Anollés "Amplifying DNA with Arbitrary Oligonucleotide Primers," *Cold Spring Harbor Laboratory Press*, ISSN 1054–9803, pp. 85–94 (1993).

Carothers et al., "Point Mutation Analysis in a Mammalian Gene: Rapid Preparation of Total RNA, PCR Amplification of cDNA, and Taq Sequencing by a Novel Method," *494 BioTechniques*, vol. 7, pp. 494–499 (date unknown).

Chen et al. "Template–Directed Dye–Terminator Incorporation (TDI) Assay: A Homogeneous DNA Diagnostic Method Based on Fluorescence Resonance Energy Transfer," *Nucleic Acids Research*, vol. 25, No. 2, pp. 347–353 (1997).

Chen et al., "Fluorescence Energy Transfer Detection as a Homogeneous DNA Diagnostic Method," *Proc. Natl. Acad. Sci.*, vol. 97, pp. 10756–10761 (Sep. 1997).

Exact Laboratories, Inc. "Search Report" (EXT–016PC) (Sep. 13, 1999—date of mailing).

Fu et al., "A DNA Sequencing Strategy That Requires Only Five Bases of Known Terminal Sequence for Priming," *Proc. Natl. Acad. Sci. USA*, pp. 10162–10166 (1995).

Hasegawa et al., "Detection of K–ras mutations in DNAs isolated from feces of patients with colorectal tumors by mutant–allele–specific amplification (MASA)," *Oncogene*, vol. 10, 8 pages (1995).

Ikonen et al., "Quantitative Determination of Rare mRNA Species by PCR and Solid–phase Minisequencing," *Cold Spring Harbor Laboratory Press*, ISSN 1054–8903, pp. 234–240 (1992).

Kieleczawa et al., "DNA Sequencing by Primer Walking with Strings of Contiguous Hexamers," *Science*, 258: pp. 1787–1791 (Dec. 11, 1992).

Kotler et al., (1993) "DNA Sequencing: Modular Primers Assembled from a Library of Hexamers or Pentamers," *Proc. Natl. Acad. Sci. USA*, 90: pp. 4241–4245 (May 1993).

Krook et al., "Rapid and simultaneous detection of multiple mutations by pooled and multiplex single nucleotide primer extension: application to the study of insulin–responsive glucose transporter and insulin receptor mutations in non––insulin–dependent diabetes," *Human Molecular Genetics*, vol. 1, No. 6, pp. 391–395 (1992).

Ph Lebacq, "Polymerase chain reaction and other methods to detect hot–spot and multiple gene mutations," *Advances in Clinical Biology*, vol. 50, pp. 709–712 (1992).

Runnebaum et al., "Multiplex PCR Screening detects small p53 deletions and insertions in human ovarian cancer cell lines," *Human Genetics*, vol. 93, pp. 620–624 (1994).

Sambrook J. et al., "Molecular cloning," Second edition, p. 13.67–13.69, (1989).

Shumaker et al., "Mutation Detection by Solid Phase Primer Extension," *Human Mutation*, vol. 7, pp. 346–354 (1996).

Syvänen, "Detection of Point Mutations in Human Genes by the Solid–phase Minisequencing Method," *Clinica Chimica Acta*, vol. 226, pp. 225–236 (1994).

Ugozzoli, et al., "Detection of Specific Alleles by Using Allele–Specific Primer Extension Followed by Capture on Solid Support," *GATA* 9(4): pp. 107–112 (1992).

Boom et al., "Rapid and Simple Method for Purification of Nucleic Acids, *Journal of Clinical Microbiology*," vol. 28, No. 3, pp. 495–503 (1990).

Giacona et al., "Cell–Free DNA in Human Blood Plasma: Length Measurements in Patients with Pancreatic Cancer and Healthy Controls," *Pancreas*, vol. 17, No. 1, pp. 89–97 (1998).

Hollstein et al., "p53 Mutations in Human Cancers," *Science*, vol. 253, pp. 49–53 (Jul. 5, 1991).

Nikiforov et al., "Genetic Bit Analysis: a solid phase method for typing single nucleotide polymorphisms," *Nucleic Acids Research*, vol. 22, No. 20, pp. 4167–4175, (1994).

Sidransky et al., "Identification of p53 Gene Mutations in Bladder Cancers and Uring Samples," *Science*, vol. 252, pp. 706–709 (May 1991).

Syvänen, :Solid–Phase Minisequencing, "Detection of Mutations and Polymorphisms in DNA," Chapter 6, pp. 53–64 (1997).

Aaltonen et al. (1994) "Replication Errors in Benign and Malignant Tumors from Hereditary Nonpolyposis Colorectal Cancer Patients" *Cancer Research* 54: 1645–1648.

Aaltonen et al. (1998) "Incidence of Hereditary Nonpolyposis Colorectal Cancer and the Feasibility of Molecular Screening for the Disease" *The New England Journal of Medicine* 338: 1481–1487.

Ausubel et al., (1995), *Short Protocols in Molecular Biology*, 3d ed., pp. 2–3—2–12, 3–30—3–33.

Bertario et al. (1999) "Risk of Colorectal Cancer Following Colonoscopic Polypectomy" *Tumori* 85: 157–162.

Blum H.E., (1995) "Colorectal Cancer: Future Population Screening for Early Colorectal Cancer" *European Journal of Cancer*, vol. 31A, pp. 1369–1372.

Bos et al., (May 28, 1987) "Prevalence of ras Gene Mutations in Human Colorectal Cancers," *Nature*, vol. 327, pp. 293–297.

Caldas et al., (Jul. 1, 1994) "Detection of K–ras Mutations in the Stool of Patients with Pancreatic Adenocarcinoma and Pancreatic Ductal Hyperplasia" *Cancer Research*, vol. 54, pp. 3568–3573.

Capozzi et al. (1999) "Evaluation of the Replication Error Phenotype in Relation to Molecular and Clinicopathological Features in Hereditary and Early Onset Colorectal Cancer" *European Journal of Cancer* 35: 289–295.

Cave et al., (1994) "Reliability of PCR Directly from Stool Samples: Usefulness of an Internal Standard," *BioTechniques*, vol. 16, No. 5, pp. 809–810.

Chapelle (1999) "Testing Tumors for Microsatellite Instability" *European Journal of Human Genetics* 7: 407–408.

Charlesworth et al., (Sep. 15, 1994) "The Evolutionary Dynamics of Repetitive DNA in Eukaryotes," *Nature*, vol. 371, pp. 215–220.

Chen et al. (1997) "Microsatellite Instability in Sporadic––Colon–Cancer Patients With and Without Liver Metastases" *International Journal of Cancer* 74: 470–474.

Coll et al., (Oct. 1989) "Evaluation of a Rapid Method of Extracting DNA from Stool Samples for Use in Hybridization Assays," *Journal of Clinical Microbiology*, vol. 27, No. 10, pp. 2245–2248.

Coughlin et al. (1999) "Public Health Perspectives on Testing for Colorectal Cancer Susceptibility Genes" *American Journal of Preventive Medicine* 16: 99–104.

Cunningham C. and M. G. Dunlop, (1996) "Molecular Genetic Basis of Colorectal Cancer Susceptibility," *British Journal of Surgery*, vol. 83, pp. 321–329.

Deng et al., (Dec. 20, 1996) "Loss of Heterozygosity in Normal Tissue Adjacent to Breast Carcinomas," *Science*, vol. 274, pp. 2057–2059.

Deuter et al., (1995) "A Method for Preparation of Fecal DNA Suitable for PCR," *Nucleic Acids Research*, vol. 23, No. 18, pp. 3800–3801.

Dib et al., (Mar. 14, 1996) "A Comprehensive Genetic Map of the Human Genome Based on 5,264 Microsatellites," *Nature* vol. 380, pp. 152–154.

Duffy M.J., (1995) "Can Molecular Markers Now be Used for Early Diagnosis of Malignancy?" *Clin. Chem,.* vol. 41, No. 10, pp. 1410–1413.

Eguchi et al., (Apr. 15, 1996) "Mutations of the p53 Gene in the Stool of Patients with Resectable Colorectal Cancer," *Cancer Supplement*, vol. 77, No. 8, pp. 1707–1710.

Enari et al., (Jan. 1, 1998) "A Caspase–Activated DNase that Degrades DNA During Apoptosis, and its Inhibitor ICAD," *Nature*, vol. 391, pp. 43–50.

Fearon, E.R., (1995) "16 Molecular Abnormalities in Colon and Rectal Cancer," *The Molecular Basis of Cancer*, pp. 340–357.

Frangi et al., "Nonsense Mutations Affect C1 Inhibitor Messenger RNA Levels in Patients with Type I Hereditary Angioneurotic Edema," *J. Clinical Invest*. 88: 755–759.

Grossman et al. (1988), "Colonoscopic Screening of persons With Suspected Risk Factors for Colon Cancer" *Gastroenterology* 94: 395–400.

Gyllensten U. B., Allen M., (1995) "Sequencing of In Vitro Amplified DNA," *Recombinant DNA Methodology II*, (Wu, ed.), pp. 565–578.

Hasegawa et al., (1995) "Detection of K–ras Mutations in DNAs Isolated From Feces of Patients with Colorectal Tumors by Mutant–Allele–Specific Amplification (MASA)," *Oncogene*, vol. 10, pp. 1441–1445.

Hoang et al. (1997) "BAT–26, an Indicator of the Replication Error Phenotype in Colorectal Cancers and Cell Lines" *Cancer Research* 57: 300–303.

Honchel et al., (1995) "Genomic Instability in Neoplasia," *Seminars in Cell Biology*, vol. 6, pp. 45–52.

Hoss et al., (Sep. 17, 1992) "Excrement Analysis by PCR" *Scientific Correspondence* pp. 199.

Iino et al. (1999) "DNA Microsatellite Instability in Hyperplastic Polyps, Serrated Adenomas, and Mixed Polyps: a Mild Mutator Pathway for Colorectal Cancer?" *Journal of Clinical Pathology* 52: 5–9.

Iniesta et al. (1998) "Genetic Abnormalities and Microsatellite Instability in Colorectal Cancer" *Cancer Detection and Prevention* 22: 383–395.

Ishimaru et al. (1995) "Microsatellite Instability in Primary and Metastatic Colorectal Cancers" *International Journal of Cancer* 64: 153–157.

Iwaya et al. (1998) "Infrequent Frameshift Mutations of Polynucleotide Repeats in Multiple Primary Cancers Affecting the Esophagus and Other Organs" *Genes, Chrom & Cancer* 23: 317–322.

Jarvinen et al. (1995) "Screening Reduces Colorectal Cancer Rate in Families With Hereditary Nonpolyposis Colorectal Cancer" *Gastroenterology* 108: 1405–1411.

Jernvall et al. (1999) "Microsatellite Instability: Impact on Cancer Progression in Proximal and Distal Colorectal Cancers" *European Journal of Cancer* 35: 197–201.

Jessup J.M. and G.E. Gallick, (Sep./Oct. 1992) "The Biology of Colorectal Carcinoma," *Current Problems in Cancer* pp. 263–328.

Jonsson et al., (Jan. 1995) "From Mutation Mapping to Phenotype Cloning," *Proc. Natl. Acad. Sci.*, vol. 92, pp. 83–85.

Kim et al. (1998) "Microsatellite Instability in Young Patients With Colorectal Cancer" *Pathology International* 48:586–594.

Konishi et al. (1996) "Molecular Nature of Colon Tumors in Hereditary Nonpolyposis Colon Cancer, Familial Polyposis, and Sporadic Colon Cancer" *Gastroenterology* 111: 307–317.

Lamberti et al. (1999) "Microsatellite Instability—a Useful Diagnostic Tool to Select Patients at High Risk for Hereditary Non–Polyposis Colorectal Cancer: A Study in Different Groups of Patients With Colorectal Cancer" *Gut* 44: 839–843.

Lengauer et al., (Dec. 17, 1998) "Genetic Instabilities in Human Cancers," *Nature*, vol. 396, pp. 643–649.

Leong et al., (1993) "Detection of MYCN Gene Amplification and Deletions of Chromosome 1p in Neuroblastoma by In Situ Hybridization Using Routine Histologic Sections," *Laboratory Investigations*, vol. 69, No. 1, pp. 43–50.

Lin et al. (1998) "Colorectal and Extracolonic Cancer Variations in MLH1/MSH2 Hereditary Nonpolyposis Colorectal Cancer Kindreds and the General Population" *Diseases of the Colon & Rectum* 41: 428–433.

Litia et al., (1992) "Simultaneous Detection of Two Cystic Fibrosis Alleles Using Dual–Label Time–Resolved Fluorometry," *Molecular and Cellular Probes*, vol. 6, pp. 505–512.

Lleonart et al. (1998) "Microsatellite Instability and p53 Mutations in Sporadic Right and Left Colon Carcinoma" *American Cancer Society* 83: 889–895.

Loktionov A. and I. K. O'Neill, (1995) "Early Detection of Cancer–Associated Gene Alterations in DNA Isolated from Rat Feces During Intestinal Tumor Induction with 1,2–Dimethylhydrazine," *International Journal of Oncology*, vol. 6, pp. 437–445.

Loktionov et al., (Feb., 1998) "Quantitation of DNA from Exfoliated Colonocytes Isolated from Human Stool Surface as a Novel Noninvasive Screening Test for Colorectal Cancer," *Clinical Cancer Research*, vol. 4, pp. 337–341.

Mao L. et al., (Feb. 2, 1996) "Molecular Detection of Primary Bladder Cancer by Microsatellite Analysis," *Science*, vol. 271, pp. 659–662.

Myers, R.M., (Feb. 12, 1993) "The Pluses of Subtraction," *Science*, vol. 259, pp. 942–943.

Naber S. P., (Dec. 1, 1994) "Molecular Pathology—Detection of Neoplasia," *New England Journal of Medicine*, vol. 331, No. 22, pp. 1508–1510.

Nollau et al., (May 1996) "Isolation of DNA from Stool and Bodily Fluids for PCR Amplication," *BioTechniques*, vol. 20, No. 5, pp. 784–788.

Nollau et al., (1996) "Detection of K–ras Mutations in Stools of Patients with Colorectal Cancer by Mutant–Enriched PCR," *Int. J. Cancer*, vol. 66 pp. 332–336.

Orlow I., et al., (Oct. 18, 1995) "Deletion of the p16 and p15 Genes in Human Bladder Tumors *Journal of the National Cancer Institute*, ,"vol. 87, No. 20, pp. 1524–1529.

Park et al. (1999) "Gene–Environment Interaction in Hereditary Nonpolyposis Colorectal Cancer with Implications for Diagnosis and Genetic Testing" *International Journal of Cancer* 82: 516–519.

Peltomaki et al. (1997) "Mutations Predisposing to Hereditary Nonpolyposis Colorectal Cancer: Database and Results of a Collaborative Study" *Gastroenterology* 113: 1146–1158.

Pharmacia, (1998) *BioDirectory*, pp. 104–109.

Pharmacia, (1991/1992) *Molecular and Cell Biology Catalogue*, pp. 8.3–8.6.

Piao et al., (Sep. 1997) "Relationship between Loss of Heterozygosity of Tumor Suppressor Genes and Histologic Differentiation in Hepatocellular Carcinoma," *Cancer*, vol. 80, No. 5, pp. 865–872.

Ponz de Leon et al. (1998) "Frequency and Type of Colorectal Tumors in Asymptomatic High–Risk Individuals in Families with Hereditary Nonpolyposis Colorectal Cancer" *Cancer Epidemiology, Biomarkers & Prevention* 7: 639–641.

Ponz de Leon et al. (1999) "Heriditary Colorectal Cancer in the General Population: From Cancer Registration to Molecular Diagnosis" *Gut* 45: 32–38.

Pyatt et al. (1999) "Polymorphic Variation at the BAT–25 and BAT–26 Loci in Individuals of African Origin" *American Journal of Pathology* 155: 349–353.

Raff, M., (Nov. 12, 1998) "Cell Suicide for Beginners," *Nature*, vol. 396, pp. 119–122.

Rashid et al. (1999) "Genetic Epidemiology of Mutated K–ras Proto–Oncogene, Altered Suppressor Genes, and Microsatellite Instability in Colorectal Adenomas" *Gut* 44: 826–833.

Ravelingien et al., (1995) "Contribution of Molecular Oncology in the Detection of Colorectal Carcinomas," *Acta Gastro–Enterologica Belgica*, vol. 58, pp. 270–273.

Riegler et al. (1999) "Prevalence of HNPCC in a Series of Consecutive Patients on the First Endoscopic Diagnosis of Colorectal Cancer: A Multicenter Study" *Endoscopy* 31: 337–341.

Rhyu M. S., (Mar. 6, 1996) "Molecular Mechanisms Underlying Hereditary Nonpolyposis Colorectal Carcinoma," *Journal of the National Cancer Institute*, vol. 88, No. 5, pp. 240–251.

Ridanpaa et al., (1995) "Detection of Loss of Heterozygosity in the p53 Tumor Suppressor Gene Using a PCR–based Assay," *Path. Res. Pract.*, vol. 191, pp. 399–402.

Rodriguez–Bigas et al. (1997) "A National Cancer Institute Worship on Hereditary Nonpolyposis Colorectal Cancer Syndrome: Meeting Highlights and Bethesda Guidelines" *Journal of the National Cancer Institute* 89: 1758–1762.

Salahshor et al. (1999) "Microsatellite Instability in Sporadic Colorectal Cancer is Not an Independent Prognostic Factor" *British Journal of Cancer* 81: 190–193.

Samowitz et al. (1995) "Microsatellite Instability in Human Colonic Cancer Is Not a Useful Clinical Indicator of Familial Colorectal Cancer" Gastroenterology 109: 1765–1771.

Samowitz et al. (1997) "Microsatellite Instability in Colorectal Adenomas" *Gastroenterology* 112: 1515–1519.

Samowitz et al. (1999) "BAT–26 and BAT–40 Instability in Colorectal Adenomas and Carcinomas and Germline Polymorphisms" *American Journal of Pathology* 154: 1637–1641.

Sanger et al., (Dec. 1977) "DNA Sequencing with Chain-Terminating Inhibitors" *Proc. Natl. Acad. Sci. USA*, vol. 74, No. 12, pp. 5463–5467.

Segel I., (1976), "Double Label Analysis," *Biochemical Calculations*, 2d ed., pp. 373–376.

Shitoh et al., (1998), "Important Microsatellite Markers in the Investigation of RER in Colorectal Cancers," *Jpn. J. Cli, Oncol*, vol. 28, No. 8, pp. 538–541.

Sidransky, et al., (Apr. 3, 1992) "Identification of ras Oncogene Mutations in the Stool of Patients with Curable Colorectal Tumors," *Science*, vol. 256, pp. 102–105.

Smith–Ravin et al., (1995) "Detection of c–Ki–ras Mutations in Faecal Samples from Sporadic Colorectal Cancer Patients," *Gut*, vol. 36, pp. 81–86.

Syngal et al. (1998) "Benefits of Colonoscopic Surveillance and Prophylactic Colectomy in Patients With Hereditary Nonpolyposis Colorectal Cancer Mutations" *Annals of Internal Medicine* 129: 787–796.

Syngal et al. (1999) "Interpretation of Genetic Test Results for Hereditary Nonpolyposis Colorectal Cancer" *JAMA* 282: 247.

Takeda et al., (1993) "Detection of K–ras Mutation in Sputum by Mutant–Allele–Specific Amplification (MASA)," *Human Mutation*, vol. 2, pp. 112–117.

Thibodeau et al., (May 7, 1993) "Microsatellite Instability in Cancer of the Proximal Colon," *Science*, vol. 260, pp. 816–819.

Vasen et al. (1993) "Surveillance in Hereditary Nonpolyposis Colorectal Cancer: An International Cooperative Study of 165 Families" *Diseases of the Colon & Rectum*) 36: 1–4.

Vasen et al. (1998) "A Cost–Effectiveness Analysis of Colorectal Screening of Hereditary Nonpolyposis Colorectal Carcinoma Gene Carriers" *American Cancer Society* 82: 1632–1637.

Vasen et al. (1999) "New Clinical Criteria for Hereditary Nonpolyposis Colorectal Cancer (HNPCC, Lynch Syndrome) Proposed by the International Collaborative Group on HNPCC" *Gastroenterology* 116: 1453–1456.

Villa et al., (May 1996) "Identification of Subjects at Risk for Colorectal Carcinoma Through a Test Based on K–ras Determination in the Stool," *Gastroenterology*, vol. 110, No. 5, pp. 1346–1353.

Vogelstein, B. and Kinzler, K.W., (Aug., 1999) "Digital PCR," *Proc. Natl. Acad. Sci. USA*, vol. 96, pp. 9236–9241.

Wallace et al., (1979) "Hybridization of Synthetic Oligodeoxyribonucleotides to $\Phi\chi$ 174 DNA: the Effect of Single Base Pair Mismatch," *Nucleic Acids Research*, vol. 6, No. 11, pp. 3543–3557.

Walsh et al., (Feb. 6, 1992) "Preferential PCR Amplification of Alleles: Mechanisms and Solutions," *PCR Methods and Applications*, pp. 241–250.

Wang et al., (May 15, 1998) "Large–Scale Identification, Mapping, and Genotyping of Singlee–Nucleotide Olymorphisms in the Human Genome," *Science*, vol. 280, pp. 1077–1082.

Watson et al., "Isolation of Differentiality Expressed Sequence Tags from Human Breast Cancer," *Advances in BriefXP 000576043*, pp. 4598–4602.

Wijnen et al. (1999) "Familial Endometrial Cancer in Femal Carriers of MSH6 Germline Mutations" *Nature Genetics* 23: 142–144.

Young G.P., and B.H. Demediu, (1992) "The Genetics, Epidemiology, and Early Detection of Gastrointestinal Cancers" *Current Opinion in Oncology*, vol. 4, pp. 728–735.

Zhou et al. (1997) "Allele Profiles of Mononucleotide Repeat Microsatellites in Control Individuals and in Colorectal Tumors With and Without Replication Errors" *Oncogene* 15: 1713–1718.

Zhou et al. (1998) "Determination of the Replication Error Phenotype in Human Tumors Without the Requirement for Matching Normal DNA by Analysis of Mononucleotide Repeat Microsatellites" *Genes, Chromosomes & Cancer* 21: 101–107.

Andreas Braun et al., "Improved Analysis of Microsatellites Using Mass spectrometry" *Genomics*, (1997) vol. 46, pp. 18–23.

Ragnhild A. Lothe, et al., "The APC Gene I1307K Variant is Rare in Norwegian Patients with Familial and Sporadic Colorectal or Breast Cancer" *Cancer Research*, (Jul. 15, 1998), vol. 58, pp. 2923–2924.

Viviana Gismondi et al., "Characterization of 19 Novel and Sic Recurring APC Mutations in Italian Adenomatous Polyposis Patients, Using Two Different Mutation Detection Techniques" *Human Mutation* (1997) vol. 9, No. 4, pp. 370–373.

\* cited by examiner

|  | KRAS | APC | P53 | BAT26 | Q | RESULTS |
|---|---|---|---|---|---|---|
| CANCER N=21 | (4) A46 A59 A5 A54 | (5) A74 A54 A76 A57 A16 | (3) A74 A82 A49 | (4) A9 A5 A6 C943 | (14) A58 A59 A46 A5 A61 A54 A74 A76 A77 A81 A82 A51 A33 A16 | SENSITIVITY 90% (19 OF 21) |
| ADENOMA N=9 | (0) | (3) N466 C899 N767 | (0) | (0) | (5) C835 C902 N767 C935 N159 | SENSITIVITY 78% (7 OF 9) |
| NORMAL N=10 | (0) | (0) | (0) | (0) | (0) | SPECIFICITY 100% (10 OF 10) |

NOTE: RESULTS ARE UNALTERED IF KRAS EXCLUDED

Fig. 3

RESULTS
EXCLUDING KRAS

| | APC | P53 | BAT26 | IQ | RESULTS |
|---|---|---|---|---|---|
| CANCER N=8 | (2) A74 A16 | (1) A82 | (2) C943 C1227 | (5) A33 A82 A74 A61 | SENSITIVITY: 89% (7 OF 8) |
| ADENOMA N=2 | (0) | (0) | (0) | (1) N739 | SENSITIVITY: 50% (1 OF 2) |
| NORMAL N=18 | (0) | (0) | (0) | (0) | SPECIFICITY: 100% (18 OF 18) |

Fig. 5

RESULTS INCLUDING KRAS

| | KRAS | APC | P53 | BAT26 | IQ | RESULTS |
|---|---|---|---|---|---|---|
| CANCER N=8 | (2) A46 A74 | (2) A74 A16 | (1) A82 | (2) C943 C1227 | (5) A33 A82 A74 A61 | SENSITIVITY 100% (8 OF 8) |
| ADENOMA N=2 | (1) N772 | (0) | (0) | (0) | (1) N739 | SENSITIVITY 100% (2 OF 2) |
| NORMAL N=18 | (2) N726 N778 | (0) | (0) | (0) | (0) | SPECIFICITY 89% (16 OF 18) |

Fig. 6

<223> BAT-26, WHEREIN EACH "n" CORRESPONDS TO A
NUCLEOTIDE OF UNKNOWN IDENTITY

<400> 37

```
ccagtggtat agaaatcttc gatttttaaa ttcttaattt taggttgcag tttcatcact 60
gtctgcggta atcaagtttt tagaactctt atcagatgat tccaactttg gacagtttga 120
actgactact tttgacttca gccagtatat gaaattggat attgcagcag tcagagccct 180
taacctttt caggtaaaaa aaaaaaaaaa agggttaaaa atgtttgattg 240
gttaannnnn nnngacagat agtgaagaag gagctaaaag gcttagaaag agttcgacat 300
caatattaga caag                                                 314
```

Fig. 7

SEQUENCE LISTING

```
<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
```

<223> OTHER INFORMATION: Description of Artificial Sequence:Primer 1

<400> SEQUENCE: 1
agcccttaac cttttcagg                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Primer 2

<400> SEQUENCE: 2
gcccttaacc tttttcaggt                                                   20

<210> SEQ ID NO 3
<211> LENGTH: 9
<212> TYPE: DNA
<213> ORGANISM: Homo sapiens
<220> FEATURE:
<223> OTHER INFORMATION: wild-type APC sequence at codon 1309

<400> SEQUENCE: 3 gaaaagatt                                                                9

<210> SEQ ID NO 4
<211> LENGTH: 5
<212> TYPE: DNA
<213> ORGANISM: Homo sapiens
<220> FEATURE:
<223> OTHER INFORMATION: typical deletion at APC codon 1309

<400> SEQUENCE: 4 gaaaa                                                                    5

<210> SEQ ID NO 5
<211> LENGTH: 5
<212> TYPE: DNA
<213> ORGANISM: Homo sapiens
<220> FEATURE:
<223> OTHER INFORMATION: typical deletion found at APC codon 1309

<400> SEQUENCE: 5 aaaag                                                                    5

<210> SEQ ID NO 6
<211> LENGTH: 5
<212> TYPE: DNA
<213> ORGANISM: Homo sapiens
<220> FEATURE:
<223> OTHER INFORMATION: typical deletion found at APC codon 1309

<400> SEQUENCE: 6 aaaga                                                                    5

<210> SEQ ID NO 7
<211> LENGTH: 314
<212> TYPE: DNA
<213> ORGANISM: Artificial Sequence
<220> FEATURE:
<223> OTHER INFORMATION: Description of Artificial Sequence:BAT-26
<223> OTHER INFORMATION: wherein each "n" corresponds to a nucleotide of
      unknown identity

<400> SEQUENCE: 7
ccagtggtat agaaatcttc gattttaaa ttcttaattt taggttgcag tttcatcact         60

-continued

```
gtctgcggta atcaagtttt tagaactctt atcagatgat tccaactttg gacagtttga    120
actgactact tttgacttca gccagtatat gaaattggat attgcagcag tcagagccct    180
taaccttttt caggtaaaaa aaaaaaaaaa aaaaaaaaaa agggttaaaa atgttgattg    240
gttaannnnn nnngacagat agtgaagaag gcttagaaag gagctaaaag agttcgacat    300
caatattaga caag                                                      314
```

METHODS FOR DETECTING MUTATIONS USING PRIMER EXTENSION FOR DETECTING DISEASE

RELATED APPLICATIONS

This application is a divisional application of U.S. Ser. No. 09/757,949, filed on Jan. 10, 2001, which is a continuation in part of U.S. application Ser. No. 09/371,991 filed Aug. 11, 1999 now U.S. Pat. No. 6,280, 947 and U.S. application Ser. No. 09/468,670 filed Dec. 21, 1999 abandoned, which claims the benefit of No. 60/134,711 filed Jan. 10,1999, the disclosures of each of which is incorporated by reference herein.

FIELD OF THE INVENTION

The invention relates generally to methods of detecting cancer, precancer, or other diseases or disorders using nucleic acid markers.

BACKGROUND OF THE INVENTION

Numerous diseases are associated with disruptions in genomic stability. For example, sickle cell anemia, phenylketonuria, hemophilia, cystic fibrosis, and various cancers have been associated with one or more genetic mutation(s). Cancer is thought to arise from a multi-step process that typically involves multiple genetic mutations leading to uncontrolled cell growth. Many cancers are curable if detected early in their development. For example, colorectal cancers typically originate in the colonic epithelium, and are not extensively vascularized (and therefore not invasive) during early stages of development. The transition to a highly-vascularized, invasive and ultimately metastatic cancer commonly takes ten years or longer. If the presence of cancer is detected prior to extensive vascularization, surgical removal typically is an effective cure. However, colorectal cancer is often detected only upon manifestation of clinical symptoms, such as pain and bloody stool. Generally, such symptoms are present only when the disease is well established, and often after metastasis has occurred. Similarly, with the exception of the Pap smear for detection of pre-malignant cervical lesions, diagnostic screening methods for other types of cancer are best at detecting established disease. Increased knowledge of the molecular basis for disease has lead to a proliferation of screening assays capable of detecting disease-associated nucleic acid mutations.

A variety of detection methods have been developed which exploit sequence variations in DNA using enzymatic and chemical cleavage techniques. A commonly-used screen for DNA polymorphisms consists of digesting DNA with restriction endonucleases and analyzing the resulting fragments by means of Southern blots, as reported by Botstein et al., *Am. J Hum. Genet.*, 32: 314–331 (1980) and White et al., *Sci. Am.*, 258: 40–48 (1988). Mutations that affect the recognition sequence of the endonuclease will preclude enzymatic cleavage at that site, thereby altering the cleavage pattern of the DNA. Thus, a difference in restriction fragment lengths is indicative of the presence of a mutation in the recognition sequence. A problem with this method (known as restriction fragment length polymorphism mapping or RFLP mapping) is its inability to detect a mutation outside of the recognition sequence and which, consequently, does not affect cleavage with a restriction endonuclease. One study reported that only 0.7% of the mutational variants estimated to be present in a 40,000 base pair region of human DNA were detected using RFLP mapping. Jeffreys, *Cell*, 18: 1–18 (1979).

Single-base mutations have been detected by differential hybridization techniques using allele-specific oligonucleotide probes. Saiki et al., *Proc. Natl. Acad. Sci.*, 86: 6230–6234 (1989). Mutations are identified on the basis of the higher thermal stability of the perfectly-matched probes as compared to mismatched probes. Disadvantages of this approach for mutation analysis include the requirement for optimization of hybridization for each probe, and the limitations imposed by the nature of the mismatch and the local sequence on the degree of discrimination of the probes. In practice, tests based only on parameters of nucleic acid hybridization function poorly when the sequence complexity of the test sample is high (e.g., in a heterogeneous biological sample). This is due partly to the small thermodynamic differences in hybrid stability generated by single nucleotide changes. Therefore, nucleic acid hybridization is generally combined with some other selection or enrichment procedure for analytical and diagnostic purposes.

Recently, a number of genetic mutations, including alterations in the BAT-26 segment of the MSH2 mismatch repair gene, the p53 gene, the Kras oncogene, and the APC tumor suppressor gene have been associated with the multi-step pathway leading to cancer. The BAT-26 segment contains a long poly-A tract. In certain cancers, a characteristic 5 base pair deletion occurs in the poly-A tract. Detection of that deletion may provide diagnostic information. For example, it has been suggested that mutations in those genes might be a basis for molecular screening assays for the early stages of certain types of cancer. See e.g., Sidransky, et al., *Science*, 256: 102–105 (1992). Attempts have been made to identify and use nucleic acid markers that are indicative of cancer. However, even when such markers are found, using them to screen patient samples, especially heterogeneous samples, has proven unsuccessful either due to an inability to obtain sufficient sample material, or due to the low sensitivity that results from measuring only a single marker. For example, simply obtaining adequate human DNA from one type of heterogeneous sample (stool) has proven difficult. See Villa, et al., *Gastroenterol.*, 110: 1346–1353 (1996) (reporting that only 44.7% of all stool specimens, and only 32.6% of stools from healthy individuals produced sufficient DNA for mutation analysis). Other reports in which adequate DNA has been obtained have reported low sensitivity in identifying a patient's disease status based upon a single cancer-associated mutation. See Eguchi, et al., *Cancer*, 77: 1707–1710 (1996) (using a p53 mutation as a marker for cancer).

Therefore, there is a need in the art for high-sensitivity, high-specificity assays for the detection of molecular indicia of cancer, pre-cancer, and other diseases or disorders, especially in heterogeneous samples. Accordingly, the invention provides methods for detecting deletions in genomic regions, such as BAT-26 and others, which may be associated with disease.

SUMMARY OF THE INVENTION

Methods of the invention provide assays for identification of a mutation in a genomic region suspected to be indicative of disease. In general, methods of the invention comprise annealing a primer upstream of a region in which, for example, a deletion is suspected to occur, extending the primer through the region, terminating extension at a known end-point, and comparing the length and/or weight of the extended primer with that of an extended primer from the corresponding wild-type (non-affected) region or a molecular weight standard (either known or run in parallel). Also according to the invention, assays described herein are combined with invasive detection methods to increase sensitivity of detection.

Methods of the invention further provide for the determination of whether a target point mutation is present at a genetic locus of interest. In one embodiment, the invention comprises contacting a nucleic acid in a biological sample with a primer that is complementary to a portion of a genetic locus, extending the primer in the presence of a labeled nucleotide that is complementary to a target nucleotide suspected to be present at the target position. The primer is further extended in the presence of a terminator nucleotide that is complementary to a nucleotide downstream from the target nucleotide, but is not complementary to the target nucleotide, thereby generating an extension product. The presence of a labeled nucleotide in the extension product is indicative of the presence of the target point mutation at the genetic locus.

In addition, methods of the invention provide for the identification of a target single nucleotide polymorphic variant present at a genetic locus of interest. In one embodiment, the method comprises contacting a nucleic acid in a biological sample with a primer, extending the primer in the presence of at least a first and a second differentially labeled nucleotide, the first labeled nucleotide being complementary to a first nucleotide suspected to be present at said target position, the second labeled nucleotide being complementary to a second nucleotide alternatively suspected to be present at the target position. The primer is further extended in the presence of a terminator nucleotide that is complementary to a nucleotide downstream from the target position, wherein the terminator nucleotide is not complementary to the first or second nucleotides, thereby generating an extension product. The identity of the labeled nucleotide present in the extension product is indicative of the identity of the target single nucleotide polymorphic variant present at the genetic locus.

In yet another embodiment, the first labeled nucleotide comprises a first acceptor molecule and the second labeled nucleotide comprises a second acceptor molecule with the first acceptor molecule being different from the second acceptor molecule. Also, the primer comprises a donor molecule being capable of activating the first and second acceptor molecules so as to produce a first and a second detectable signal.

Furthermore, the methods of the invention provide the determination of whether a target single nucleotide polymorphic variant is present at a genetic locus of interest. For example, the method comprises contacting a nucleic acid in a biological sample with a primer, extending the primer in the presence of a labeled nucleotide that is complementary to a nucleotide suspected to be present at the target position, further extending the primer in the presence of a terminator nucleotide that is complementary to a nucleotide downstream from the target nucleotide, wherein the terminator nucleotide is not complementary to the target nucleotide, thereby to produce an extension product; and determining whether the labeled nucleotide is present in the extension product, thereby determining whether the target single nucleotide polymorphic variant is present at the genetic locus.

Moreover, the methods of the invention provides the quantification of the number of a nucleic acid having a target nucleotide present at a genetic locus of interest In general, the method comprises contacting a nucleic acid in a biological sample with a primer, extending the primer in the presence of a labeled nucleotide that is complementary to target nucleotide, further extending the primer in the presence of a terminator nucleotide that is complementary to a nucleotide downstream from the target nucleotide, wherein the terminator nucleotide is not complementary to the target nucleotide, thereby to form an extension product, and enumerating the number of extension products that comprise the labeled nucleotide, thereby determining the number of nucleic acids having the target nucleotide at the genetic locus.

In preferred embodiments, an extended primer produced in methods of the invention is labeled downstream of the region suspected to contain a mutation. In a preferred embodiment, the comparative length and/or molecular weight of the extended primer is determined by gel electrophoresis or mass spectroscopy. Also in a preferred embodiment, the region suspected to contain the mutation comprises a poly-nucleotide tract in which a deletion is suspected to occur, and the sequence immediately downstream of the region is known and does not repeat a nucleotide species present in the polynucleotide tract. Preferably, the polynucleotide tract comprise three, two, or preferably one, species of nucleotide as explained in detail below. Methods of the invention retain the specificity of primer extension assays while increasing their sensitivity by reducing background due to premature termination of the extension reaction. Therefore, methods of the invention provide a highly sensitive and highly specific assay for detecting a small amount of mutant nucleic acid in a heterogeneous sample of predominantly wild-type nucleic acid.

Methods of the invention provide screening assays for the detection of a deletion in a region of the genome comprising at least one, but no more than three, species of nucleotide, and that is characterized by having a sequence for primer hybridization immediately upstream, and a sequence immediately downstream that does not contain a nucleotide present in the region suspected to be deleted. In a preferred embodiment, methods of the invention comprise selecting a nucleic acid having a known wild-type sequence and having a region (the deletion of which is suspected in disease) comprising at most three different types of nucleotides; hybridizing an oligonucleotide primer, or pair of oligonucleotide primers, immediately upstream of the target region; extending the primer by using a polymerase in the presence of the nucleotide bases that are complementary to the nucleotide bases of the target region, thereby to form a primer extension product; further extending the primer extension product in the presence of a labeled nucleotide that is complementary to a nucleotide base downstream from the target region, but not complementary to a nucleotide base within the target region; and determining the size of the extension product compared to a standard (e.g., a wild-type product or a molecular weight standard).

For purposes of the present invention a "mutation" includes a deletion, addition, substitution, transition, transversion, rearrangement, and translocation in a nucleic acid, as well as a loss of heterozygosity. A loss of heterozygosity is a form of mutation in which all or a portion of one allele is deleted. Also for purposes of the present invention, the terms "markers", "targets", and "mutations" include nucleic acid (especially DNA) mutations, as well as other nucleic acid indicia useful in methods of the invention, such as specific alleles and single nucleotide polymorphism variants. Such indicia also include the amount of amplifiable nucleic acid in a sample, the integrity and/or length of nucleic acids in a sample, the ratio of high integrity nucleic acids (greater tan about 200 base pairs) to low integrity nucleic acids (less than about 200 base pairs), and any other nucleic acid variations that differ between patients with cancer and disease-free patients.

In a preferred embodiment, the target region in which a deletion is suspected to occur is greater than five nucleotides long, and/or the deletion is greater than three nucleotides long. In a preferred embodiment, the primer extension reactions are cycled by varying the reaction temperature through successive annealing, extending and denaturing temperatures. Preferably, the molecular weight standard is the wild-type extension product, or one that corresponds to the expected size for the extension product from the wild-type nucleic acid template. The presence of an extension product smaller than the molecular weight standard is indicative of the presence of a deletion in the target region of the nucleic acid template. In a preferred embodiment, the primer extension product is terminated by incorporating a terminator nucleotide that is complementary to a nucleotide downstream from the target region in a wild type nucleic acid, but not complementary to any of the nucleotides of the target region. In a more preferred embodiment, the labeled nucleotide and the terminator nucleotide are the same. In an alternative embodiment, more than one labeled nucleotide base is incorporated into the extension product prior to incorporation of the terminator nucleotide. Preferably, the nucleotides incorporated during extension through the region suspected of containing a deletion are unlabeled. However, if those nucleotides are labeled, they are preferably distinguishable from the labeled nucleotide that is incorporated at the 3' end of the extension product.

In a preferred embodiment, methods of the invention comprise detecting a nucleic acid mutation in a biological sample, such as stool, urine, semen, blood, sputum, cerebrospinal fluid, pus, or aspirate, that contains a heterogeneous mixture of nucleic acid having a deletion in the target region and wild type nucleic acid. Such a mutation in the target region may be present in only about 1–5% of the nucleic acid molecules having the target region. To increase the sensitivity of the assay, the sample may comprise a polymerase chain reaction product. Method of the invention are particularly useful in analyzing a deletion in the target region that is indicative of the presence of cancerous or precancerous tissue in such a biological sample, including colorectal cancer or precancer detection in stool. In another embodiment, methods of the invention comprise further extending the primer extension product in the presence of labeled and unlabeled nucleotides, the nucleotides being of the same type (i.e., A, T, C, or G) and being complementary to one or more nucleotide downstream from the target region but not complementary to a nucleotide within the target region. In one embodiment, the ratio of the labeled nucleotide to unlabeled nucleotide is 1:1. Methods of the invention may also include incorporating more than one monomer of the labeled nucleotide or unlabeled nucleotide into the extension product.

In another embodiment, methods of the invention comprise detecting a deletion in a sample by selecting a nucleic acid with a known wild-type sequence and having a target region suspected of containing a deletion, wherein the target region contains at most three different types of nucleotide bases selected from the group consisting of dGTP, dATP, dTTP, and dCTP; hybridizing an oligonucleotide primer to a region upstream of said target region in a nucleic acid sample; contacting said hybridized oligonucleotide primer with an extension reaction mixture comprising: i) nucleotides which are complementary to the nucleotides in the target region, ii) a labeled nucleotide which is complementary to a nucleotide found downstream from the target region, but which is not complementary to any nucleotide base found within the target region, and iii) a terminator nucleotide which is complementary to a nucleotide found downstream from the target region, but which is not complementary to any nucleotide found in the target region; extending the hybridized oligonucleotide primer to generate a labeled extension product; and comparing the size of the labeled extension product to a molecular weight standard, wherein a labeled extension product smaller than the molecular weight standard is indicative of the presence of a deletion in the target region.

In another embodiment, methods of the invention comprise single base extension assays that detect low-frequency molecular events in a biological sample. Methods for detecting low-frequency molecular events in a biological sample are provided in U.S. Pat. No. 4,683,202, the disclosure of which is incorporated by reference herein. Specific nucleic acids may be detected in a biological sample with both high sensitivity and high specificity. In general, methods of the invention comprise performing a single-base extension reaction utilizing donor and acceptor molecules which interact to produce a detectable signal.

The nucleotides comprise an acceptor molecule which interacts with a donor molecule on the primer when in close proximity and thus facilitates detection of the extended primers, or extended short first probes in an extension reaction. The donor and acceptor molecules may comprise a fluorophore. In preferred embodiments, the donor and acceptor molecules comprise a fluorescent dye such 6-carboxyfluorescein (FAM, Amersham), 6-carboxy-X-rhodamine (REG, Amersham), $N_1$, $N_1$ $N^1$, $N^1$-tetramethyl-6-carboxyrhodamine (TAMARA, Amersham), 6-carboxy-X-rhodomine (ROX, Amersham), fluorescein, Cy5® (Amersham) and LightCycler-Red 640 (Roche Molecular Biochemicals). In a preferred embodiment, the donor molecules comprise FAM and the acceptor molecules comprise REG, TAMARA or ROX. In an alternate embodiment, the donor is fluoroscein and the acceptor is Cy5® or LightCycler-Red 640 (Roche Molecular Biochemicals). Alternatively, the donor and acceptor molecules comprise fluorescent labels such as the dansyl group, substituted fluorescein derivatives, acridine derivatives, coumarin derivatives, pthalocyanines, tetramethylrhodamine, Texas Red®, 9-(carboxyethyl)-3-hydroxy-6-oxo-6H-xanthenes, DABCYL®, BODIPY® (Molecular Probes, Eugene, Oreg.) can be utilized. Such labels are routinely used with automated instrumentation for simultaneous high throughput analysis of multiple samples.

Fluorescence monitoring of amplification is based on the concept that a fluorescence resonance energy transfer occurs between two adjacent fluorophores and a measurable signal is produced. When an external light source, such as a laser or lamp-based system is applied, the donor molecule is excited and it emits light of a wavelength that in turn excites an acceptor molecule that is in close proximity to the donor molecule. The acceptor molecule then emits an identifiable signal (i.e., a fluorescent emission at a distinct wavelength) that can measured and quantified. The donor molecule does not transmit a signal to acceptor molecules that are not in close proximity. Thus, when the ddNTP incorporates into the primer, the donor and acceptor molecules are brought close together and a fluorescence energy transfer occurs between the two fluorophores causing the acceptor molecule to emit a detectable signal. Acceptor molecules that are in close proximity to donor molecule emit a signal that is distinctly different from the acceptor molecules alone (i.e., an acceptor molecule that is not in proximity with the donor). In addition, multiple different acceptor molecules may be used, in which each acceptor "combines" with the same donor molecule to produce distinct signals, each being characteristic of a specific donor-acceptor combination. Monitoring the fluorescence emission from the acceptor fluorophore after excitation of the donor fluorophore allows highly sensitive product analysis.

Methods of the invention are especially useful to detect indicia of cancer or precancer in a heterogeneous sample. Stool is a good example of a heterogeneous sample in which methods of the invention are useful. A typical stool sample contains patient nucleic acids, but also contains heterologous nucleic acids, proteins, and other cellular debris consistent with the lyric function of the various nucleases, proteinases and the like found in the colon. Under normal circumstances, stool solidifies as it proceeds from the proximal colon to the distal colon. As the solidifying stool passes through the colon, colonic epithelial cells are sloughed onto the stool. If a patient has a developing tumor or adenoma, cells from the tumor or adenoma will also be sloughed onto stool. Those cells, and/or their debris, will contain molecular indicia of disease (e.g., mutations or loss of heterozygosity). In the early stages of development, nucleic acid indicative of an adenoma or tumor comprise only about 1% of the nucleic acid in a voided stool. If left untreated, proportionately more disease-related nucleic acids are found in stool. Methods of the invention are useful for detecting early-stage lesions in heterogeneous samples such as stool. Methods of the invention result in a high degree of sensitivity and specificity for the detection of early-stage disease. Methods of the invention are especially useful in detecting, for example, adenomas in the colon. Adenomas are non-metastatic lesions that frequently have the potential for metastasis. If all adenomas in a patient are detected and removed, the probability of complete cure is virtually certain.

The methods of the present invention also exploit the discovery that mutations in the BAT-26 segment of the MSH2 mismatch repair gene are closely associated with inherited cancers (and pre-cancerous lesions). In particular, BAT-26 mutations are highly-associated with Hereditary Non-Polyposis Colorectal Cancer ("HNPCC") (i.e., in greater than 90% of patients), making BAT-26 an ideal marker for screening assays to detect this colorectal cancer, or colorectal adenoma that may or may not develop into cancer. Use of methods of the invention on the BAT-26 locus identifies the characteristic deletions by producing an extension product in affected DNA that is shorter than the expected wild-type extension product. Methods of the invention will be exemplified below using the BAT-26 locus. However, methods of the invention are appreciated to be useful on any genetic locus in which a deletion occurs. Especially useful loci are those correlated with disease, and especially cancer.

Furthermore, BAT-26 mutations have been found to be associated with cancers located in the right-hand (proximal) side of the colon. Thus, the methods of the present invention contemplate utilizing a combinatorial testing approach to screen patients, wherein BAT-26 testing is used to screen the right side of the colon, and flexible sigmoidoscopy is utilized to screen the left hand (distal/lower) side of the colon. Such a testing methodology permits a far more thorough screen for cancerous and/or precancerous lesions than was previously possible using tests practiced in the art. Thus, in another embodiment, the present invention provides methods for detecting the presence of colorectal cancerous or precancerous lesions comprising (i) conducting in a sample obtained non-invasively or minimally-invasively from a patient an assay to identify a BAT-26 marker in the sample, and (ii) performing a flexible sigmoidoscopy on the patient.

The methods of the invention are useful for detecting diseases or disorders related to the colon including, but not limited to, cancer, pre-cancer and other diseases or disorders such as adenoma, polyp, inflammatory bowel disorder, inflammatory bowel syndrome, regional enteritis, granulomatous ileitis granulomatous ileocolitis, Crohn's Disease, ileitis, ileocolitis, jejunoileitis, granulomatous colitis, Yersinia enterocolitica enteritis, ulcerative colitis, psuedomembraneous colitis, irritable bowel syndrome, diverticulosis, diverticulitis, intestinal parasites, infectious gastroenteritis, toxic gastroenteritis, and bacterial gastroenteritis.

The methods of the present invention also provide for the use of BAT-26 as a marker for detection of cancerous and precancerous lesions by analysis of heterogeneous samples (e.g., stool). Such methods comprise obtaining a representative sample of a stool voided by a patient and performing an assay on the sample to identify a BAT-26 marker in the sample.

In another preferred embodiment, methods of the invention comprise selecting one or more mutational events that are indicative of cancer, precancer, or other diseases or disorders, such that the combined informativeness of the one or more events meets or exceeds a predetermined or desired level of informativeness. The informativeness of any mutation or combination of mutations may be validated by an accepted invasive screening technique. For example, in methods to detect colorectal cancer, the informativeness of a molecular assay may be determined by identification of a lesion using colonoscopy.

A detailed description of certain preferred embodiments of the invention is provided below. Other embodiments of the invention are apparent upon review of the detailed description that follows.

BRIEF DESCRIPTION OF THE DRAWINGS

FIG. 3 is a table showing the results of a clinical study of screening assays performed on 40 subjects using various markers, including BAT-26.

FIGS. 5 and 6 are tables showing the results of a clinical study of screening assays performed on 28 subjects using various markers, including BAT-26.

FIG. 7 depicts the DNA sequence on the BAT-26 locus (SEQ ID NO: 7), wherein each "n" corresponds to a nucleotide of unknown identity.

DETAILED DESCRIPTION OF THE INVENTION

Figure 1A:
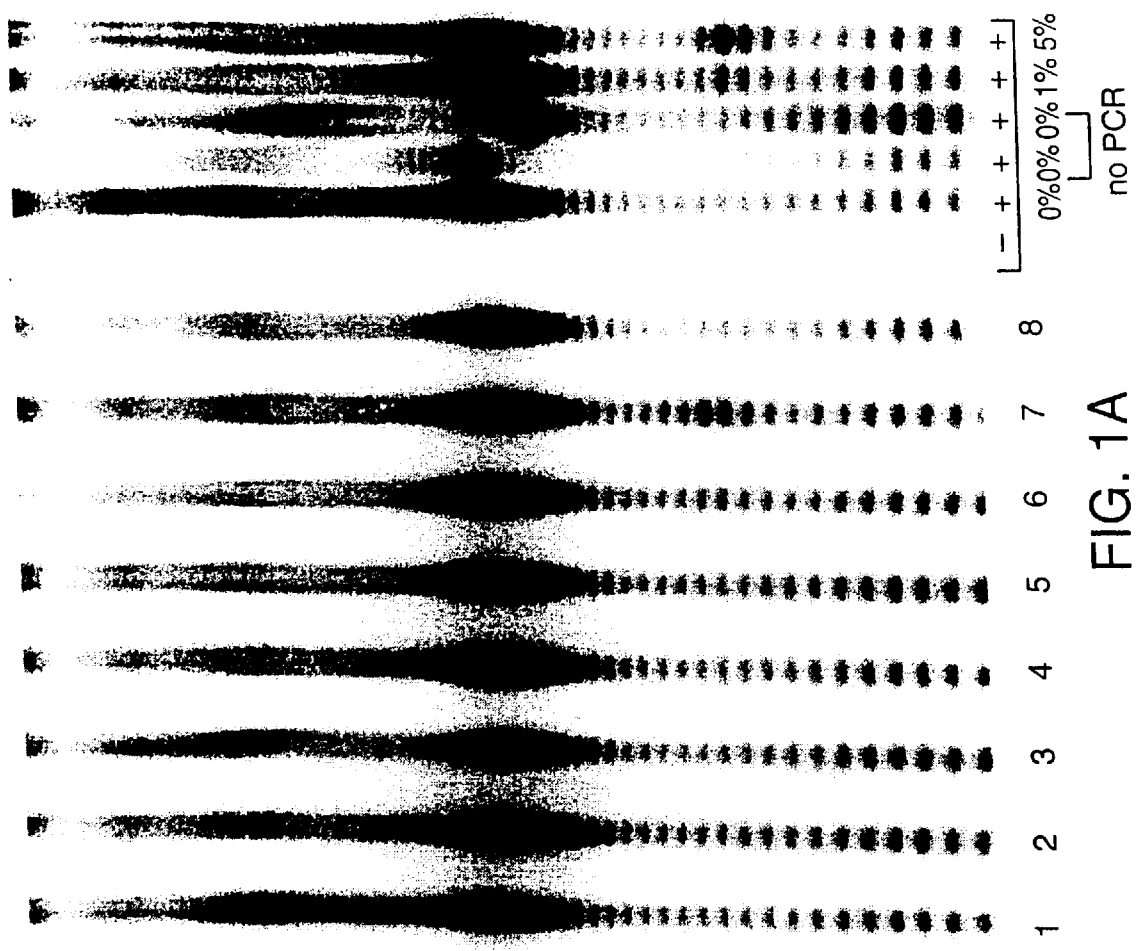
FIG. 1A shows BAT-26 deletion detection using primer extension reactions that incorporate labeled bases before the 3' end of the extension product.

Methods of the invention provide non-invasive or minimally-invasive and highly sensitive assays for detecting the presence of mutations in nucleic acid samples for the detection of early stage cancer, precancer, or other diseases or disorders. Methods of the invention also provide non-invasive or minimally invasive and highly sensitive assays for determining the presence of other indicia such as specific alleles or variants in nucleic acid samples for the detection of early stage cancer, precancer or other diseases or disorders. Methods of the invention are especially useful for detecting the presence of nucleic acid deletions and/or insertions in heterogeneous biological samples to detect disease such as cancer or precancer. In preferred embodiments, methods of the invention are useful to detect mutations at loci that are associated with a disease such as cancer by identifying in a patient sample one or more nucleic acid mutations(s) that provide high sensitivity and high specificity for detection of the indicia of cancer or precancer. Methods of the invention comprise identifying mutations having a known informativeness for cancer or precancer, or may be based upon validating selected mutations or assays to detect them with respect to a standard assay for cancer. Preferred methods comprise assays utilizing detection of BAT-26 mutations. By utilizing cancer or precancer markers having a high sensitivity/specificity for detecting the presence of cancer or precancer, methods of the invention provide improvements in non-invasive or minimally-invasive molecular screening assays. For purposes of the present invention, non-invasive or minimally-invasive indicates that specimens for analysis are selected from the group consisting of stool, sputum, blood, urine, bile, cerebrospinal fluid, seminal fluid, saliva, aspirate, pancreatic juice, and the like. However, any tissue or body fluid specimen may be used according to methods of the invention.

In general, methods of the invention comprise identifying a target nucleic acid region that is suspected of being mutated, and interrogating the target region using a primer extension reaction. A primer is hybridized upstream of the target region and extended through the target region. The extension reaction is terminated at a site beyond the target region. The extension product is analyzed, and the size of the product is used as an indicator of the presence or absence of a mutation in the target nucleic acid region. In general, the presence of an extension product that is smaller than expected is indicative of the presence of a deletion in the target region. Conversely, the presence of a labeled extension product that is larger than expected is generally indicative of the presence of an insertion in the target region. However, the presence of a small or large labeled extension product can also be an indicator of a point mutation in the target region, as explained in greater detail in the following sections.

Methods of the invention are particularly useful when the target region contains a sequence that causes the extending polymerase to pause, stutter, or terminate prematurely. For example, regions containing nucleotide repeats such as a tract of a given nucleotide (such as the poly-A tract at the BAT-26 locus) dinucleotide or trinucleotide repeats. However, the invention is generally useful to detect mutations at loci having a known wild-type nucleic acid.

In a preferred embodiment, a primer is hybridized upstream of a target region that contains at most three different nucleotide bases. The hybridized primer is extended through the target region in the presence of unlabeled nucleotides that are complementary to nucleotides of the target region. The primer extension product is further extended in the presence of a labeled terminator nucleotide that is complementary to a nucleotide found downstream from the target region, but not found in the target region. An extension product is only labeled if the labeled terminator nucleotide is incorporated in the extension reaction. Consequently, an extension product is only labeled if it is extended through the target region, and along to the template nucleotide that is complementary to the labeled terminator nucleotide. Accordingly, prematurely terminated extension products are not labeled and do not interfere with the detection and analysis of labeled product.

The present invention comprises embodiments wherein the primer is labeled, or wherein a labeled nucleotide is incorporated into the extension product before extension through the target region is complete, provided that an additional label is incorporated into fully extended products so that they can be distinguished from prematurely terminated extension products. In one embodiment, a primer is labeled with a first label, the labeled primer is hybridized upstream of the target region and extended through the target region, a second label is incorporated into the extension product downstream from the target region, and the extension reaction is terminated. Consequently, an extension product that terminates prematurely within the target region only contains the first label, whereas a fully extended product contains both the first and second label. Accordingly, diagnostically relevant extension products are those that contain both labels.

Methods of the invention also comprise assays in which the extension product is labeled and terminated in separate steps, after extension through the target region is complete. In one embodiment, a template nucleic acid comprises a target region consisting of a repeat of a first nucleotide base or a microsatellite region. Downstream from the target region is a second nucleotide base followed by a third nucleotide base. A primer is hybridized upstream of the target region and extended through the target region in the presence of unlabeled nucleotides that are complementary to the first nucleotide. After extension through the target region is complete, the extension product is further extended in the presence of a labeled nucleotide that is complementary to the second nucleotide of the template. Finally, the labeled extension product is terminated via an extension reaction in the presence of a terminator nucleotide (such as a dideoxy nucleotide) that is complementary to the third nucleotide of the template. Other embodiments of this aspect of the invention are also described in the following sections.

Figure 1B:
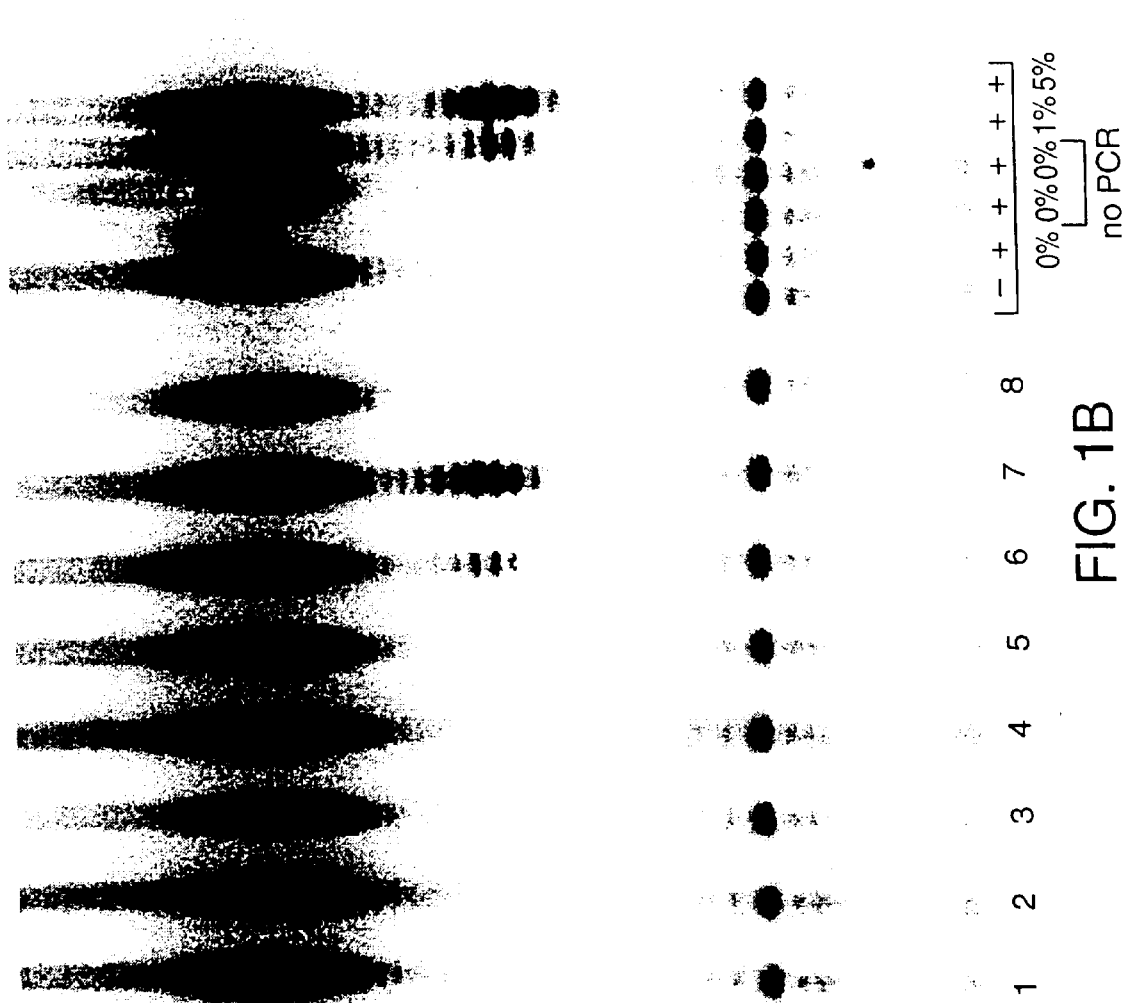
FIG. 1B shows BAT-26 deletion detection using primer extension reactions that incorporate labeled bases at the 3' end of the extension product.

Accordingly, an important aspect of the invention is a primer extension reaction wherein prematurely terminated extension products can be distinguished from complete extension products that have not undergone premature termination. Preferably, prematurely terminated extension products are not labeled, whereas complete extension products are detectably labeled. FIGS. 1A and 1B the usefulness of the invention in a deletion detection assay. The experimental details relating to FIGS. 1A and 1B are described in greater detail in Example 1. FIGS. 1A and 1B show that the invention provides an effective method for minimizing background when interrogating a target nucleic acid region suspected of containing a deletion. FIG. 1A shows multiple samples that were analyzed by a primer extension assay that incorporated labeled nucleotides into the extension product upstream of the target region. In FIG. 1B, the same samples were analyzed according to methods of the invention FIG. 1B does not contain the background of labeled prematurely terminated extension products that are seen in FIG. 1A. Consequently, the presence of a deletion is clearly indicated in lane 7 of FIG. 1B, whereas lane 7 of FIG. 1A is more difficult to interpret.

Additional aspects of the invention are described in the following sections and illustrated by the Examples.

Choosing the Target Region and the Oligonucleotide Primer

Preferably, a locus associated with a disease such as cancer is chosen. Most preferably, a locus that is known to frequently exhibit one or more deletions is chosen. Useful loci include those containing at most 3 out of the 4 possible nucleotide bases. Preferably, a chosen locus comprises a polynucleotide region in which the deletion is suspected to occur. Once a locus is chosen, primers are designed or chosen to maximize specificity of binding to a nucleotide sequence immediately upstream of the region suspected of containing a deletion. The primer must hybridize immediately upstream of the region suspected of containing the deletion so that no labeled nucleotide is incorporated into the primer extension product.

Sample Preparation and Hybridization

Methods of the invention are performed on any tissue or body fluid, including biopsy samples, and others having a high concentration of affected (i.e., mutated) cells or cellular debris. However, methods of the invention are particularly useful for detecting mutations in heterogeneous biological samples. A preferred sample is stool. For the analysis of stool samples, preferred methods of the invention comprise obtaining at least a cross-section or circumferential portion of a voided stool as taught in U.S. Pat. No. 5,741,650, and co-pending, co-owned U.S. patent application Ser. No. 09/059,718, both of which are incorporated by reference herein. While a cross-sectional or circumferential portion of stool is desirable, methods provided herein are conducted on random samples obtained from voided stool, which include smears or scrapings. Once obtained, the stool specimen is homogenized. A preferable buffer for homogenization is one that contains at least 16 mM ethylenediaminetetraacetic acid (EDTA), as taught in co-pending, co-owned U.S. patent application Ser. No. 60/122,177, incorporated by reference herein. It has been discovered that the use of at least 100 mM EDTA, and preferably 150 mM EDTA greatly improves the yield of nucleic acid from stool. Thus, a preferred buffer for stool homogenization comprises phosphate buffered saline, 20–100 mM NaCl or KCl, at least 100 mM EDTA, and optionally a detergent (such as SDS) and a proteinase (e.g., proteinase K).

After homogenization, nucleic acid is preferably isolated from the stool sample. Isolation or extraction of nucleic acid is not required in all methods of the invention, as certain detection techniques can be adequately performed in homogenized stool without isolation of nucleic acids. In a preferred embodiment, however, homogenized stool is spun to create a supernatant containing nucleic acids, proteins, lipids, and other cellular debris. The supernatant is treated with a detergent and proteinase to degrade protein, and the nucleic acid is phenol-chloroform extracted. The extracted nucleic acids are then precipitated with alcohol. Other techniques can be used to isolate nucleic acid from the sample. Such techniques include hybrid capture, and amplification directly from the homogenized stool. Nucleic acids can be purified and/or isolated to the extent required by the screening assay to be employed.

Nucleic acids to be analyzed are chosen based upon known or suspected relationships between specific sequences and cancer or precancer. Such sequences may comprise a mutation, or a specific allele or variant. If desired, sequence-specific hybrid capture is used to isolate specific nucleic acids from the sample. Target nucleic acids may be analyzed by any method of the art. Examples of preferred methods include enumerative analysis of a loss of heterozygosity as taught in U.S. Pat. No. 5,670,325, incorporated by reference herein. Enumerative methods compare the number in a sample of a wild-type nucleic acid known not to be altered in cancer or precancer with the number of a wild-type nucleic acid known or suspected to be altered in cancer or precancer. A statistically-significant difference in the two numbers indicates a positive screen.

Target nucleic acids may also be analyzed by single base extension techniques to identify, for example, a single nucleotide variant or point mutation indicative of cancer or precancer. Preferably, single base extension assay are cycled as taught in co-owned, co-pending U.S. patent application Ser. No. 09/067,212, incorporated by reference herein. Briefly, cycled single base extension reactions comprise annealing a nucleic acid primer immediately 5' to a region containing a single base to be detected. The single base to be detected represents a marker for a mutation. The mutation may be, for example, a single point mutation or a larger mutation for which the single base is a marker. Two separate reactions are conducted. In the first reaction, primer is annealed to target, and labeled (preferably with $^{32}P$) nucleic acids complementary to non-wild type (e.g. mutants indicative of disease) variants at the single base to be detected, and unlabeled dideoxy nucleic acids complementary to the wild-type base are combined. Primer extension is stopped the first time a wild-type (dideoxy) base is added to the primer. Presence of label in the extended primer is indicative of the presence of a mutation. In a second reaction, the positive control contains labeled nucleic acid complementary to the wild-type base in the presence of the primer. A DNA polymerase, such as Sequenase™ (Amersham), is used for primer extension. In a preferred embodiment, a thermostable polymerase, such as Taq or thermal sequenase is used to allow more efficient cycling. Once an extension reaction is completed, the first and second probes bound to target nucleic acids are dissociated by heating the reaction mixture above the melting temperature of the hybrids. The reaction mixture is then cooled below the melting temperature of the hybrids and additional primer is permitted to associate with target nucleic acids for another round of extension reactions. In a preferred embodiment, 10 to 50 cycles of extension reactions are conducted. In a most preferred embodiment, 30 cycles of extension reactions are conducted. After completion of all cycles, extension products are isolated and detected. In alternative embodiments, chain-terminating methods other than dideoxy nucleotides may be used. For example, chain termination occurs when no additional bases are available for incorporation at the next available nucleotide on the primer.

Primer Extension, Labeling and Termination

A hybridized primer is extended through the target region using known methods for primer extension, including extension using DNA polymerases. An extended primer preferably is labeled using a detectable label. Preferably, a labeled nucleotide is added to the extended primer once extension through the target region is complete. In a preferred embodiment, the labeled extension reaction is terminated at a predetermined position downstream from the target region. In a preferred embodiment, the labeling and terminating steps are performed simultaneously. In one embodiment, a labeled terminator nucleotide is incorporated into the extended primer downstream from the target region. Alternatively, the labeling and terminating steps are performed separately. Preferably, the labeling and terminating reactions are performed at about the same predetermined site downstream from the target region. If not, premature termination of a labeled extension product can interfere with the analysis of the results. Indeed, if a labeled primer extension product must be extended significantly in order to reach the predetermined termination site, then premature termination of the labeled extension product results in a shorter than expected labeled extension product. This short extension product may result in either a false positive indication of a deletion, or creates a background that interferes with the detection of a short extension product resulting from a deletion in the target region. Preferably the labeled base is also a terminator base. More preferably the labeled base is incorporated immediately upstream of the terminator base. The label is preferably a radioactive isotope. Alternatively a fluorescent tag, a molecular weight tag or other detectable label may be used.

Detection and Analysis of the Extension Product

While unlabeled primer extension products are contemplated, in preferred methods of the invention, only extension products that have been extended through the region suspected of containing a deletion are analyzed, because they are the only extension products that contain a detectable label. Extension products that terminate prematurely within the region suspected of containing a mutation are not labeled and are not detected in the assay. Therefore, these premature extension products do not contribute to background noise that interferes with the analysis of the results.

Extended primer products are preferably detected using gel electrophoresis, mass spectroscopy, sequencing, and other methods for determining the differential length of two primers.

The following examples illustrate practice of the invention using deletion detection in the BAT-26 and APC 1309 loci on samples prepared from stool specimens.

EXAMPLE 1

Deletion Detection at the BAT-26 Locus

Experiments were conducted to demonstrate the usefulness of the invention to detect deletions in the BAT-26 locus. The following experiment compares the specificity for detecting deletions at the BAT-26 locus using primer extension reactions that incorporate label before extension through the target region versus primer extension reactions that incorporate label at the 3' end of the extension product.

The nucleic acid template was prepared as follows. Template nucleic acid containing the BAT-26 locus was amplified by PCR. To each 50 µl PCR reaction tube, 40 µl of washed streptavidin coated Dynal beads were added and mixed by vortexing on a high setting for a few seconds. The mixture was incubated in a rack at room temperature for 15 minutes, and mixed by vortexing after 5 minutes and 10 minutes of the incubation period. The tube was placed in a magnetic tube holder, and the supernatant was removed. A 100 µl aliquot of 2×binding & wash buffer was added to each sample, and vortexed on a high setting for a few seconds. The tube was again placed in a magnetic tube holder and the supernatant was removed. A 100 µl aliquot of 0.1M NaOH was added to each tube, and mixed by vortexing on high for a few seconds. After a 5 minute incubation at room temperature, the tubes were placed in a magnetic tube holder, and the supernatant was removed. A further 100 µl of 0.1 M NaOH was added, and vortexed for a few seconds. After placing the tube in a magnetic tube holder and removing the supernatant, 100 µl of 1×binding & washing buffer was added and vortexed for a few seconds on a high setting. The tube was placed in a magnetic tube holder, the supernatant was removed, and 100 µl of 1×TE pH 8.0 was added. The tube was vortexed on high for a few seconds, placed in a magnetic tube holder, and the supernatant was removed. The beads were resuspended in 100 µl of 0.1×TE pH 8.0 buffer by vortexing on high for a few seconds. The resulting samples were used in the assays, and may be stored at 4° C. for up to 1 month. In a first experiment, 5 µl of bead-bound PCR product was added to the following primer extension reaction mixture: 9.625 µl of sterile molecular biology grade diH$_2$O, 2.5 µl of 10×Sequenase Buffer, 2.5 µl of 5 uM primer 1, 2.5 µl of 2 mM dATP, 2.5 µl of 50 uM ddGTP, 0.125 µl of $^{32}$P dTTP, and 0.25 µl of Sequenase. The reaction mixture was cycled in an MJ Research Tetrad Thermalcycler according to the following temperature profile.

| Temperature | Time | # Cycles |
| --- | --- | --- |
| 94° C. | 5 min | 1 |
| 94° C. | 30 sec | |
| 52° C. | 10 sec | 30 |
| 72° C. | 10 sec | |
| 4° C. May be taken out of cycler immediately or after overnight run | | |

A 15 µl aliquot of formamide based stop solution was added to each sample and mixed by pipetting up and down 5 times. A 7 µl aliquot from each sample was analyzed using a 15% denaturing polyacrylamide gel with 7M Urea in 1×TBE running buffer. The gel was dried and analyzed using a Packard Instant Imager. Results are shown in FIG. 1A. Lanes 1–8 are analyses of DNA obtained from patient stool samples. Lanes 9–14 are controls. Lane 9 contains no DNA template. Lanes 10, 13, and 14 contain, respectively, 0%, 1%, and 5% mutant DNA with a deletion within the poly-A stretch of the BAT-26 locus. Lanes 11 and 12 are no PCR controls. In a second experiment, 5 µl of bead bound PCR product was added to the following primer extension reaction mixture: 7.125 µl of sterile molecular biology grade diH20, 2.5 µl of 10×Sequenase Buffer, 2.5 µl of 5 uM primer 2, 2.5 µl of 2 mM dATP, 2.5 µl of 50 uM ddTTP, 2.5 µl of 0.1 uM dGTP, 0.125 µl of 32P dGTP, and 0.25 µl of Sequenase.

The reaction mixture was exposed to the same temperature cycling as the reaction mixture in the first experiment, and the products were separated on a polyacrylamide gel under the same conditions. Lanes 1–14 of FIG. 1B show results of this second experiment. The same nucleic acid templates were used in the reactions shown in lanes 1–14 of FIG. 1A and lanes 1–14 of FIG. 1B.

In the first experiment, shown in FIG. 1A, the radioactive dGTP was incorporated into the primer extension product before it was extended through the poly-A stretch of the BAT-26 locus. Primer 1 (5'-AGCCCTTAACCTTTTTCAGG-3', SEQ ID No: 1) used in the first experiment, hybridizes immediately upstream of a site where dTTP is incorporated (an A on the template strand). Accordingly, prematurely terminated extension products are labeled and appear as background in all of lanes 1–8.

In the second experiment, shown in FIG. 1B, the radioactive dTTP was incorporated into the primer extension product after it was extended through the poly-A stretch of the BAT-26 locus. The 3' end of primer 2 (5'-GCCCTTAACCTTTTTCAGGT-3', SEQ ID NO: 2) used in the second experiment, includes the T that is immediately downstream from primer 1. Accordingly, in the second reaction, radioactive dTTP is only incorporated into the primer extension product after it has been extended through the poly-A stretch. Furthermore, the extension reaction is also terminated close to the site of $^{32}$P dGTP incorporation.

The second reaction mixture also contains ddTTP, and some of the extension products incorporate $^{32}$PdGTP followed by ddTTP at the T repeat downstream from the poly-A or microsatellite stretch. Accordingly, in the second experiment, primer extension products that terminate prematurely within the poly-A stretch are not labeled and are not seen as background in lanes 1–8, nor in control lanes 9–14. In FIG. 1B, only lanes 6 and 7, and control lanes 13 and 14, contain short labeled primer extension product. The only samples that contained nucleic acid template having a deletion in the poly-A stretch were the ones that were analyzed in lanes 6, 7, 13, and 14. The sample of lane 6 was contaminated with a small amount of deleted template. The sample of lane 7 was from a patient with colon cancer associated with a deletion in the poly-A stretch of the BAT-26 locus. The samples of lanes 13 and 14 contained 1% and 5% mutant DNA, respectively.

A comparison of FIGS. 1A and 1B, shows that methods of the invention reduce the background of primer extension reactions. As a result, the analysis is much easier to interpret. Indeed, the presence of smaller than expected extension products in the second experiment is an indication of the presence of mutant nucleic acid in the sample. In the first experiment, smaller than expected extension products are present in all reactions, and the analysis is more complicated.

In addition, methods of the invention, illustrated by the results of the second experiment, can be used to detect a very small amount of mutant nucleic acid in a heterogeneous sample containing mainly normal nucleic acid. The results shown in lanes 6 and 13 are the most striking. In FIG. 1A, it is difficult to decide whether a deletion product is present in lanes 6 and 13. In contrast, a deletion product is clearly present in lanes 6 and 13 of FIG. 1B.

Methods of the invention are particularly useful for analyzing loci such as BAT-26, where a stretch of repeated nucleotide sequence interferes the with efficient extension of DNA polymerase reactions. Premature termination of extension reactions is typically more frequent at such loci.

EXAMPLE 2

Deletion Detection at the APC 1309 Locus

A deletion of 5 nucleotides is often found at codon 1309 of the APC gene. The nucleotide sequence at this location is 5'-GAAAAGATT-3' (SEQ ID NO: 3) in the wild-type gene. Typical deletions consist of GAAAA (SEQ ID NO: 4), AAAAG (SEQ ID NO: 5), or AAAGA (SEQ ID NO: 6). To detect any of these deletions using a method of the invention, a 17-base oligonucleotide was designed to hybridize immediately upstream of the position of the first G (the G of the GAA codon above). Hybridized primer was extended in the presence of unlabeled dATP, unlabeled dGTP, and $^{32}$P-ddTTP. Accordingly, the extension product is only labeled if it is extended through the target region suspected of containing a deletion and the labeled ddTTP is incorporated. The expected wild-type product is 25 bases long, whereas any of the deletions described above generates a 20-base long extension product.

Figure 2:
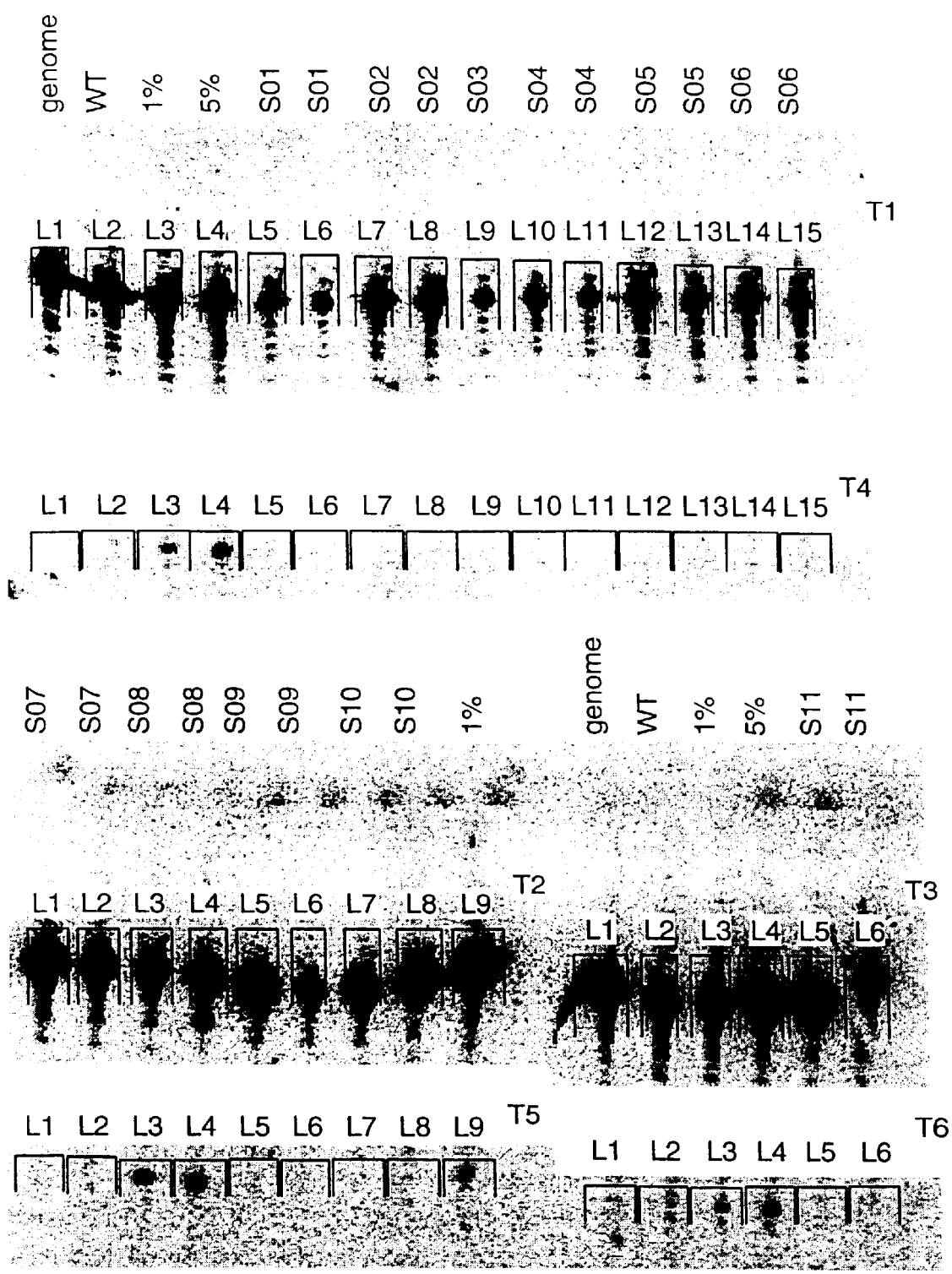
FIG. 2 shows deletion detection at the APC1309 locus.

The extension reaction was performed on a duplicates of patient samples and the results are shown in FIG. 2. Controls containing 0%, 1%, and 5% mutant nucleic acid were also analyzed that contained a 5 base pair deletion in BAT-26. The control results indicate that the presence of 1% mutant nucleic can be detected unambiguously. Both tests for patient #508 indicated the presence of a deletion at the 1309 locus. Patient # 508 did indeed have colon cancer associated with a deletion at the 1309 locus.

In contrast, the results for patients without a deletion at the 1309 locus showed no background at the position characteristic of a deletion containing extension product. Accordingly, methods of the invention are useful for a simple test for the presence of a deletion at the 1309 locus.

The invention will be exemplified further with experiments to detect the presence of indicia of colorectal cancer or precancer in samples prepared from patient stool specimens. However, the skilled artisan recognizes that methods of the invention can be practiced using a variety of different samples in order to detect a variety of cancers, pre-cancers, and other diseases and disorders.

A reason that detection of colorectal cancer or precancer (e.g., an adenoma) is exemplified is that a stool specimen is a good example of a heterogeneous environment in which methods of the invention are especially useful (see above). Moreover, colonoscopy (and sigmoidoscopy, a related technique) is a well-known invasive standard that has a high sensitivity and high specificity (although high cost and low patient compliance) with which methods of the invention can be compared and validated.

Methods of the invention comprise screening a sample, such as one prepared from a stool specimen, for the presence of one or more marker(s) of cancer, precancer, or other diseases or disorders (e.g., a colorectal tumor or adenoma), such that the sensitivity of detection is between about 50% and about 100%, and the specificity of detection is between about 85% and about 100%. In a preferred embodiment, methods of the invention combine different types of assays in order to achieve an overall increase in sensitivity and specificity. Thus, methods of the invention comprise conducting an assay for a mutation known to be associated with cancer, precancer or another disease or disorder, and an assay for a quantity and/or length of DNA expected to occur in conjunction with the cancer, precancer, or other disease or disorder in order to obtain the combined benefits of the sensitivity and specificity of both assays. Moreover, embedded within the concept of utilizing multiple nucleic acid analyses to detect a disease or disorder is the use of multiple genomic targets in each assay in order to provide further increases in sensitivity and specificity. However, as shown below, a single-marker assay is sufficient for practice of the invention.

The genomic targets and assay methods used according to the invention can vary depending upon the desired level of sensitivity and specificity, as well as the type of disease or disorder the detection of which is desired. Genomic targets (e.g., mutations) are selected based upon their known sensitivity or specificity or by determining a baseline sensitivity and specificity. In preferred embodiments, methods of the invention comprise the detection of a mutation at a single, informative locus. In other embodiments, assays for informative loci are combined in order to achieve improved sensitivity and specificity of detection relative to invasive techniques. Accordingly, methods of the invention contemplate a combination of assays selected from multiple mutation detection, quantitative polymerase chain reaction (i.e., to determine the amount of amplifiable DNA in a sample), sequence-specific hybrid capture, oligo-ligation, amplification refractory mutation system, single-stranded conformational polymorphism detection, sequencing, mismatch detection, and single base extension. Target loci include chromosomes 1, 5, 8, 17, and 18, particularly chromosome 5q, chromosome 17p, chromosome 8p, chromosome 1q, and chromosome 18q. Preferred loci for use in methods of the invention include p53, APC, BAT-26, and others suspected to be predictive of certain diseases or disorders. A preferred locus for use in methods of the invention is BAT-26.

Other genes are known to be associated with colorectal cancer, and their sensitivity and specificity are determined when not known in the literature by determining the percentage of tumors bearing the mutation, and the percentage of healthy specimens that bear the mutation from a sufficiently large and diverse population. This can be done empirically, or mathematically using algorithms that predict the likelihood of false positive and false negative screening results based upon data relating the presence of a mutation to the presence of cancer, pre-cancer or another disease or disorder. In the case of colorectal cancer, confirmation of a patient's clinical status can be accomplished by a standard test such as colonoscopy (which has a typical sensitivity of 95% and a typical specificity of 100%). The preferred method of analysis of stool samples, as discussed earlier, comprises obtaining at least a cross-section or circumferential portion of a voided stool. While a cross-sectional or circumferential portion of stool is desirable, methods provided herein are conducted on random samples obtained from voided stool, which include smears or scrapings. Once obtained, the stool specimen is homogenized in a buffer that contains at least 16 mM ethylenediaminetetraacetic acid (EDTA). However, as discussed earlier, it has been discovered that the use of at least 150 mM EDTA greatly improves the yield of nucleic acid from stool.

Methods of the invention are also useful for screening populations of patients in order to identify characteristics in population samples that are indicative of cancer or adenoma. For example, methods of the invention comprise high sensitivity, high specificity screening of populations of patients in order to correlate nucleic acid mutations or polymorphic variants present in a subset of patient samples with the presence of disease in those patients. Thus, methods of the invention comprise detecting genomic variations in patient samples, correlating those variations with confirmed disease, and using the variations associated with confirmed disease as a diagnostic screen for the disease in subsequent patient samples. Such methods preferably are performed on pooled samples, such as stool samples, from identified populations of patients (e.g., diseased, healthy). Such methods are preferably based upon variations in single nucleotide polymorphic loci. The sensitivity and specificity of detecting variants in those loci as a function of disease is determined. Those loci that predict disease at predefined levels of sensitivity and specificity are selected for use in screening assays for unknown patient samples.

BAT-26 mutations have also been found to be associated with cancers located in the right-hand (proximal) side of the colon. Thus, the methods of the present invention contemplate the use of a combinatorial testing approach to screen patients, wherein BAT-26 testing is used to screen the right side of the colon, and flexible sigmoidoscopy is utilized to screen the left hand (distal/ower) side of the colon. This type of testing methodology permits a far more comprehensive screen for cancerous and/or precancerous lesions than was practiced previously in the art.

Methods of the invention are useful not only for detecting cancer or precancer, but also for detecting other colonic diseases or disorders that may be correlated with specific nucleic acid markers including, but not limited to, adenoma, polyp, inflammatory bowel disorder, inflammatory bowel syndrome, regional enteritis, granulomatous ileitis granulomatous ileocolitis, Crohn's Disease, ileitis, ileocolitis, jejunoileitis, granulomatous colitis, Yersinia enterocolitica enteritis, ulcerative colitis, psuedo-membraneous colitis, irritable bowel syndrome, diverticulosis, diverticulitis, intestinal parasites, infectious gastroenteritis, toxic gastroenteritis, and bacterial gastroenteritis.

The following examples provide further specific exemplification of the concepts discussed above. The assays exemplified below are for purposes of illustration.

EXAMPLE 3

Clinical Study of Cancer Detection Using BAT-26 Marker

Stool specimens were collected from 40 individuals who presented at the Mayo Clinic (Rochester, Minn.) with symptoms or history indicating that a colonoscopy should be performed. Each stool sample was frozen. Immediately after providing a stool sample, all individuals were given a colonoscopy in order to determine their disease status. Colonoscopy, an invasive test requiring sedation of the patient, has a sensitivity approaching 95%, and a specificity of nearly 100% for the diagnosis of colonic neoplasia. Based upon the colonoscopy results and subsequent histological analysis of biopsy samples taken during colonoscopy, individuals were placed into one of three groups: normal, cancer, and adenoma. An adenoma, or polyp, is considered clinically relevant if it has a diameter of 1 cm or greater. Thus, all individuals in the adenoma group had a polyp of at least 1 cm in diameter. Patients in the cancer group had tumors diagnosed as cancer, and the disease-free individuals were those for whom colonoscopy showed no sign of cancer or adenoma. Based upon the colonoscopy results, 21 patients were diagnosed with cancer, 9 patients were diagnosed with an adenoma greater than 1 cm, and 10 patients were free of cancer or adenoma.

Multiple mutation analysis was then performed, on a blinded basis (i.e., scientists performing the assays did not know the results of colonoscopy or histology), on each sample. Each frozen stool specimen, weighing from 7–33 grams, was thawed, homogenized in 500 mM Tris, 16 mM EDTA, and 10 mM NaCl, pH 9.0, at a volume to mass ratio of about 3:1. Samples were then rehomogenized in the same buffer to a final volume-to-mass ratio of 20:1, and spun in glass macro beads at 2356×g. The supernatant was collected and treated with SDS and proteinase k. The DNA was then phenol-chloroform extracted and precipitated with alcohol. The precipitate was suspended in 10 mM Tris and 1 mM EDTA (1×TE), pH 7.4. Finally, the DNA was treated with Rnase.

Human DNA was isolated from the precipitate by sequence-specific hybrid capture. Biotynilated probes against portions of the p53, K-ras, and APC genes were used.

A 10 $\mu$l aliquot of each probe (20 pmol/capture) was added to a suspension containing 300 $\mu$l DNA in the presence of 310 $\mu$l 6M GITC buffer for 2 hours at room temperature. Hybrid complexes were isolated using streptavidin-coated beads (Dynal). After washing, probe-bead complexes were suspended at 25° C. for 1 hour in 0.1×TE buffer, pH 7.4. The suspension was then heated for 4 minutes at 85° C., and the beads were removed.

Captured DNA was then amplified using PCR, essentially as described in U.S. Pat. No. 4,683,202, incorporated by reference herein.

Samples were heated to 94° C. for 5 minutes, and then 40 cycles were conducted between 94° C., 60° C., and 72° C. (1 minute each), followed by one cycle at 72° C. for 5 minutes.

Amplified nucleic acid samples were then run on an electophoretic gel and size differences in the amplified PCR products were observed to detect mutant samples.

As shown in FIG. 3, four out of nineteen cancers found had BAT-26 mutations.

Figure 4:
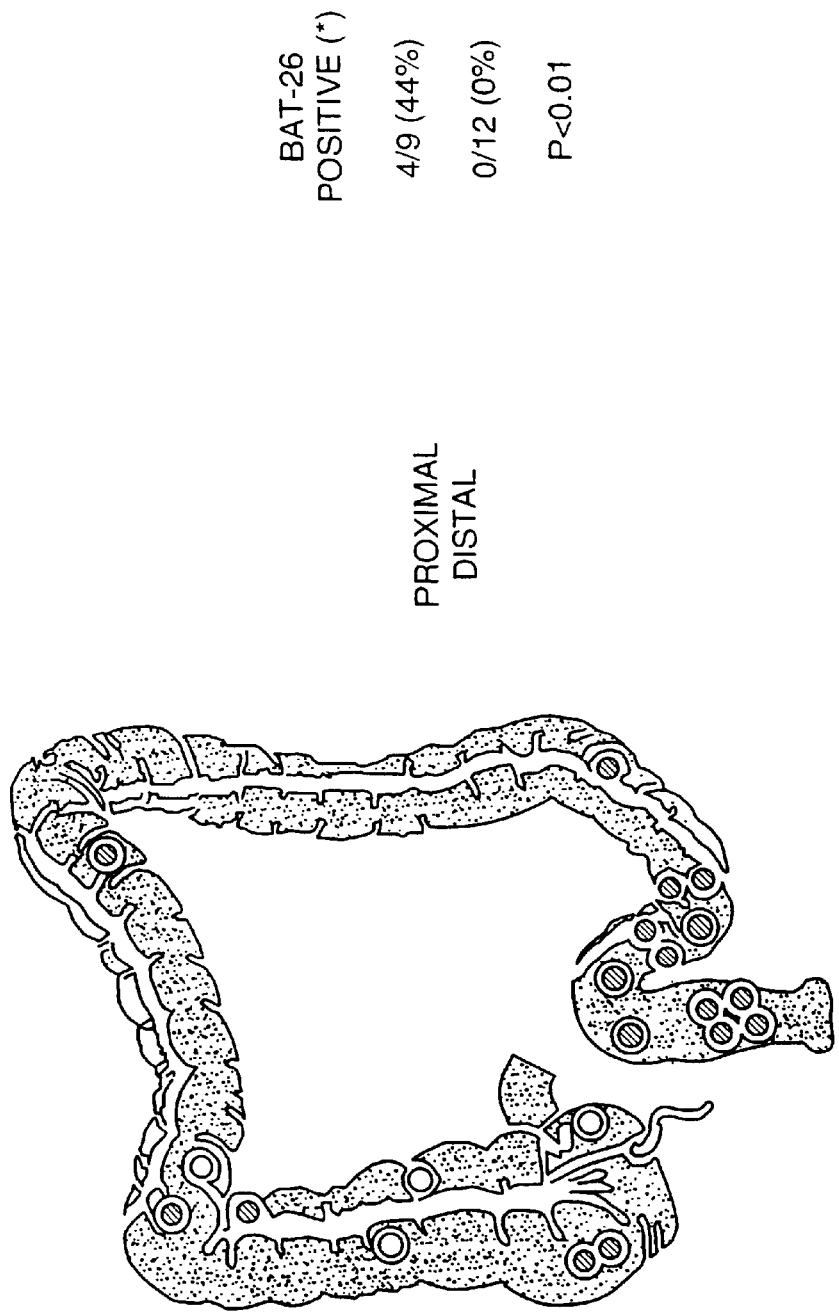
FIG. 4 is a pictorial representation of the location of nineteen cancers located in the study described in FIG. 3.

As shown in FIG. 4, all nineteen cancers were found in varying parts of the colon, but only the right-sided cancers had BAT-26 mutations.

EXAMPLE 4

Diagnostic Assay Using BAT-26

The BAT-26 mismatch repair locus (FIG. 7) was used to assess the same 40 samples described above. Deletions in BAT-26 have been associated with colorectal cancer or adenomas. Samples were prepared as described above. A primer was hybridized to the portion of the BAT-26 locus immediately upstream of the poly-A tract, which consists of 26 adenosines (nucleotides 195–221). Unlabeled deoxythymidine, a mixture of labeled and unlabeled deoxycytosine, and unlabeled dideoxyadenine were added along with polymerase. The primer was extended through the poly-A region. The labeled and unlabelled cytosine was extended for the next three bases (nucleotides 222–224, all guanines in the intact sequence) such that label was incorporated into each extended primer. After the poly-A tract and the three guanines, there exist two thymidines in the intact sequence. Thus, the dideoxyadenosine stops primer extension by addition at the end of a primer that has been extended through the poly-A and triguanine regions. Strands were separated, and the length of the strands was observed on a polyacrylamide gel to detect deletions in the poly-A tract. The results are presented below in Table A:

TABLE A

| Patient Status | Diagnosis By Colonoscopy | Diagnosis By BAT-26 Detection | Sensitivity of BAT-26 Detection | Specificity of BAT-26 Detection |
|---|---|---|---|---|
| Cancer/Adenoma | 21/9 | 4/0 | 19%/0% | 100%/0% |

As shown above, BAT-26 alone did not provide the high sensitivity achieved using multiple mutation or quantitation alone, but showed high sensitivity in comparison with other single locus detection assays. Moreover, as shown below, BAT-26 in combination with the other techniques described above produced an overall increase in sensitivity and specificity.

EXAMPLE 5

Cumulative Effects of Kras, Multiple Mutation, Quantitation, and BAT-26

The results obtained above for Kras, multiple mutation analysis, quantitation, and BAT-26 were combined to determine the cumulative effects of using combinations of those techniques in order to produce increased sensitivity and specificity in a non-invasive assay for cancer or precancer. The results are summarized below in Table B:

TABLE B

| Assay Combination | Kras and Quantitation and BAT-26 | Quantitation and BAT-26 | Multiple Mutation and Quantitation and BAT-26 |
|---|---|---|---|
| Sensitivity for Detection of Cancer/Adenoma | 80%/56% | 80%/56% | 90%/78% |
| Specificity for Detection of Cancer/Adenoma | 100% | 100% | 100% |

As shown in the summary above, the combination of multiple mutation analysis, quantitative PCR, and BAT-26 produced a sensitivity approaching that of colonoscopy. A combination of multiple mutation analysis and quantitation alone also produces very high sensitivities. All assays resulted in a specificity of 100% (no false positive results), which is comparable to colonoscopy.

The foregoing experiments show that even a single high-sensitivity/high specificity non-invasive or minimally-invasive assay produces diagnostic results that are superior to non-invasive/minimally-invasive techniques of the art, and approach results observed with the recognized standard invasive diagnostic procedure (colonoscopy). Moreover, a non-invasive assay utilizing more than one high-sensitivity/high-specificity technique results in diagnostic accuracy approaching 100%. As such, methods of the invention provide a significant improvement in the ability to perform accurate non-invasive diagnosis of cancer.

EXAMPLE 6

Clinical Study of Cancer Detection Using BAT-26 Marker

The methods described above in Example 3 were followed using stool specimens collected from 28 individuals at the Mayo Clinic (Rochester, Minn.) with symptoms or history indicating that a colonoscopy should be performed. The results are shown in FIGS. 5 and 6, and demonstrated that the study found two of eight cancers with BAT-26 mutations.

What is claimed is:

1. A method for detecting a nucleic acid insertion or deletion, the method comprising the steps of:
   (a) selecting a nucleic acid having a known wild-type sequence and having a target region comprising a polynucleotide repeat sequence having at most three different types of nucleotide bases selected from the group consisting of dGTP, dATP, dTTP, and dCTP;
   (b) contacting a sample with an oligonucleotide primer that is complementary to a portion of said nucleic acid immediately upstream of said target region;
   (c) extending said primer in the presence of nucleotide bases that are complementary to the nucleotide bases of the target region, thereby to form a primer extension product;
   (d) extending the primer extension product in the presence of a labeled nucleotide complementary to a nucleotide base downstream from the target region in said nucleic acid, wherein said labeled nucleotide is not complementary to any of the nucleotide bases of the target region selected in step (a), thereby to produce a labeled extension product comprising a sequence that is complementary to the entire target region;
   (e) detecting the labeled extension product; and
   (f) comparing the size of the labeled extension product detected in step e) to a standard, wherein a labeled extension product smaller than the standard is indicative of the presence of a deletion in the target region and a labeled extension product larger than the standard is indicative of the presence of an insertion in the target region.

2. The method of claim 1, further comprising the step of terminating the primer extension product by incorporating a terminator nucleotide in said product that is complementary to a nucleotide downstream from the target region in a wild type nucleic acid, wherein said terminator nucleotide is not complementary to any of the nucleotides of the target region selected in step (a), said step of terminating the primer extension product being performed simultaneously with or immediately after step (d).

3. The method of claim 2, wherein the labeled nucleotide and the terminator necleotide are the same.

4. The method of claim 1, wherein the labeling reaction of step (d) is performed in the presence of labeled nucleotide and unlabeled nucleotide of the same type.

5. The method of claim 4, wherein the ratio of labeled nucleotide base to unlabeled nucleotide base is 1:1.6 (unlabeled:labeled).

6. The method of claim 4, wherein more than one nucleotide from step (d) is incorporated into the labeled extension product.

7. The method of claim 1, wherein said sample contains a heterofeneous mixture of mutant nucleic acid having a deletion in the target region and wild type nucleic acid with no deletion in the target region.

8. The method of claim 1, wherein said sample is selected from the group consisting of stool, homogenized stool, urine, semen, blood, saliva, sputum, cerebrospinal fluid, pancreatic juice, pus, and a spirate.

9. The method of claim 1, wherein a deletion in the target region is indicative of the presence of cancerous or precancerous tissue in the biological sample.

10. The method of claim 1, wherein said sample includes a buffer comprising at least 100 nM DTA.

11. The method of claim 1, wherein said target region is the poly-A tract at the BAT-26 locus.

12. The method of claim 1, wherein said target region is a microstatellite region.

13. The method of claim 1, wherein the presence of a deletion in said target region is associated with the presence of a mutation at a separate genetic locus selected from the group consisting of APC, DCC, P53, and RAS.

* * * * *